US010610696B1

(12) United States Patent
Peled

(10) Patent No.: US 10,610,696 B1
(45) Date of Patent: Apr. 7, 2020

(54) APPARATUS AND METHOD FOR TREATING BIOLOGICAL TISSUE

(71) Applicant: Yona Peled, Kiryat Tivon (IL)

(72) Inventor: Yona Peled, Kiryat Tivon (IL)

(*) Notice: Subject to any disclaimer, the term of this patent is extended or adjusted under 35 U.S.C. 154(b) by 601 days.

(21) Appl. No.: 15/168,751

(22) Filed: May 31, 2016

Related U.S. Application Data

(60) Provisional application No. 62/168,875, filed on May 31, 2015.

(51) Int. Cl.
| A61N 1/40 | (2006.01) |
| A61N 1/04 | (2006.01) |
| A61N 1/36 | (2006.01) |
| A61N 1/32 | (2006.01) |
| A61N 2/00 | (2006.01) |
| A61N 5/06 | (2006.01) |
| A61N 5/067 | (2006.01) |

(52) U.S. Cl.
CPC ........... A61N 1/403 (2013.01); A61N 1/0452 (2013.01); A61N 1/0456 (2013.01); A61N 1/0484 (2013.01); A61N 1/328 (2013.01); A61N 1/36014 (2013.01); A61N 2/008 (2013.01); A61N 5/0625 (2013.01); A61N 2005/067 (2013.01)

(58) Field of Classification Search
CPC .......... A61N 1/06; A61N 1/403; A61B 5/053; A61B 5/0538; A61B 5/4519
See application file for complete search history.

(56) References Cited

U.S. PATENT DOCUMENTS

| 4,989,605 A * | 2/1991 | Rossen .............. A61N 1/36021 128/907 |
| 7,503,927 B1 * | 3/2009 | Vetanze ............... A61N 1/0408 607/115 |
| 2013/0289679 A1 * | 10/2013 | Eckhouse .............. A61N 1/403 607/102 |
| 2014/0039341 A1 * | 2/2014 | Bohorquez .......... A61B 5/0537 600/547 |

* cited by examiner

Primary Examiner — Kaitlyn E Smith
Assistant Examiner — Tigist S Demie
(74) Attorney, Agent, or Firm — Roach Brown McCarthy & Gruber, P.C.; Kevin D. McCarthy

(57) ABSTRACT

Some embodiments relate to a 2D array/chain of basic units where each basic unit is individually addressable. Each basic unit may include a rigid or semi-rigid plate—e.g. of electrically insulating material and an electrode (e.g. ball electrode)—for example, a ball-shaped electrode. The device may be used to treat biological tissue—e.g. to provide TEMS muscle stimulation.

11 Claims, 39 Drawing Sheets

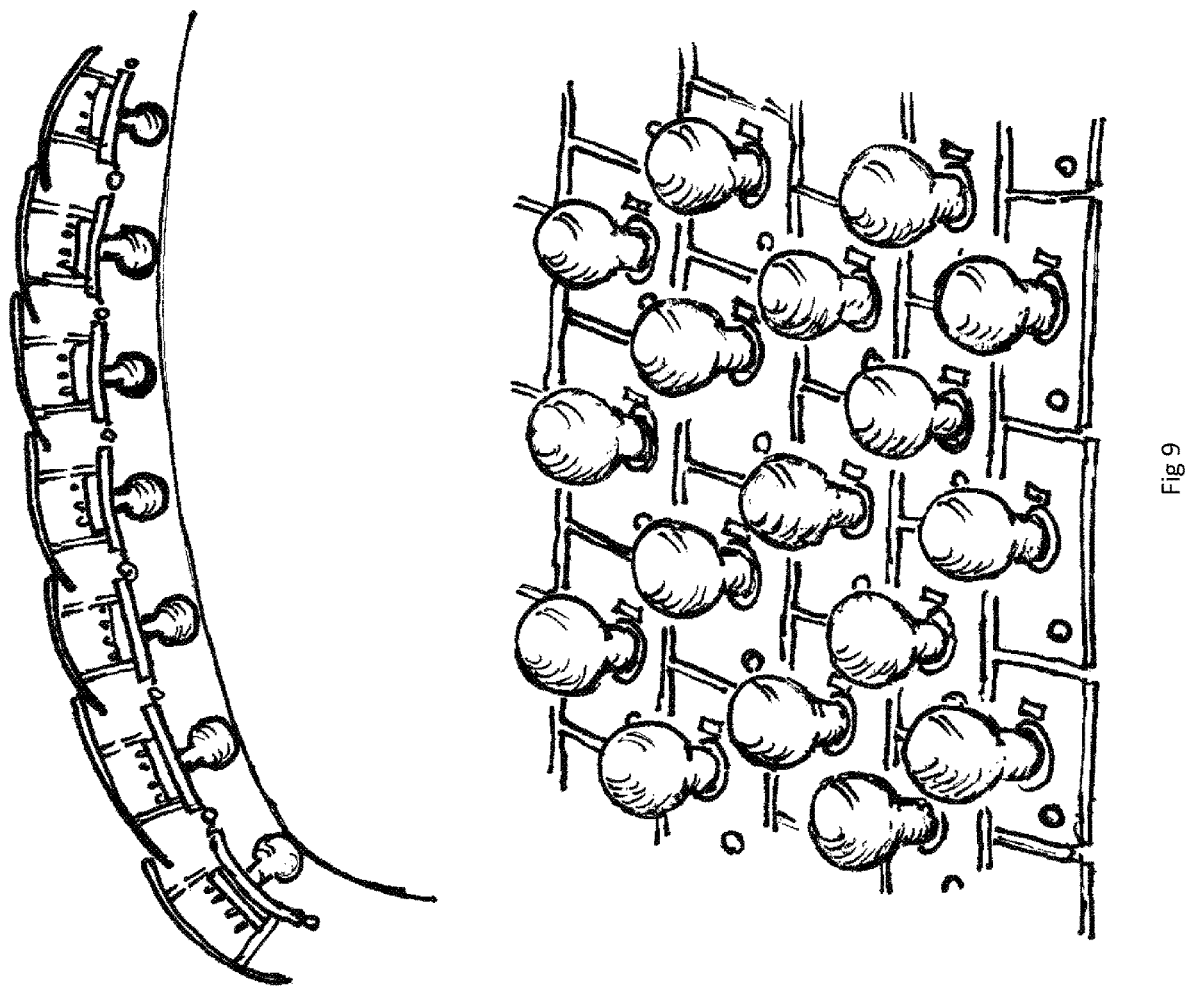

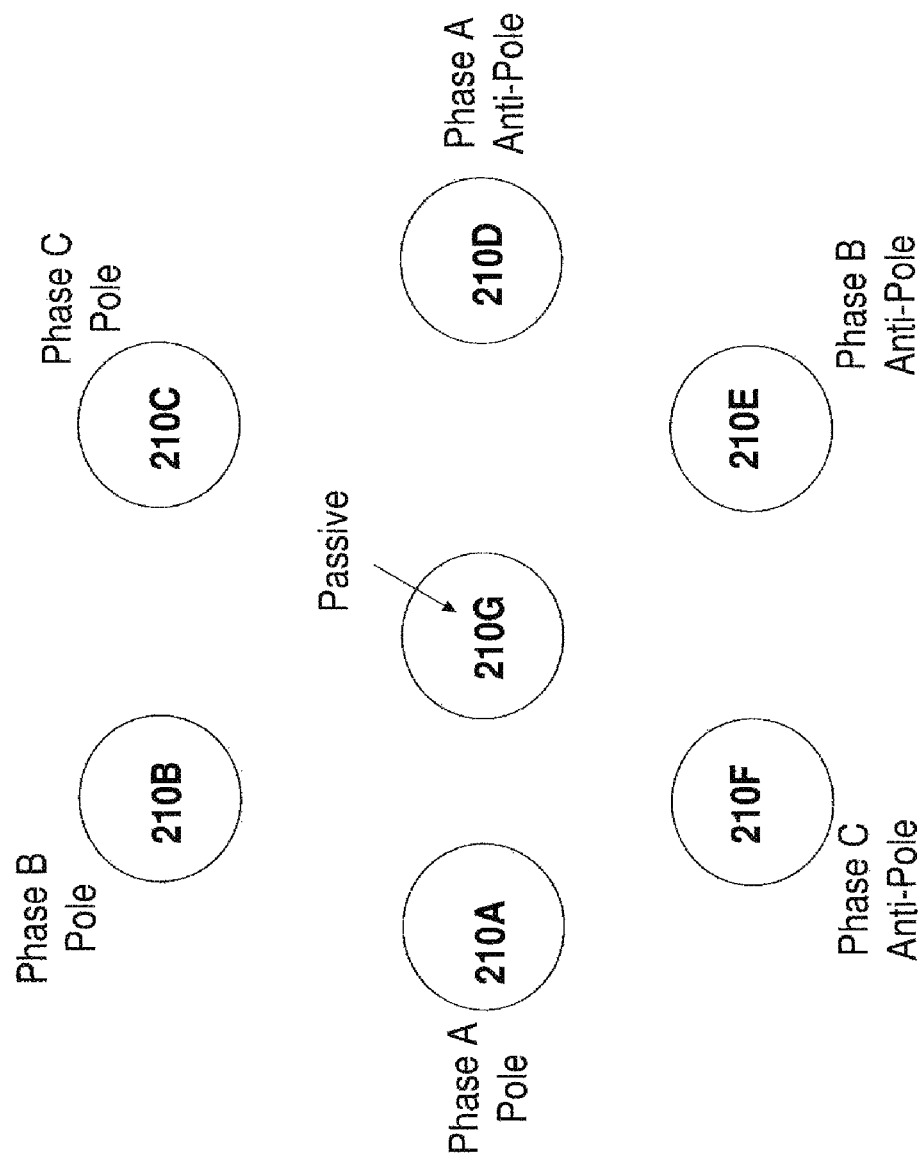

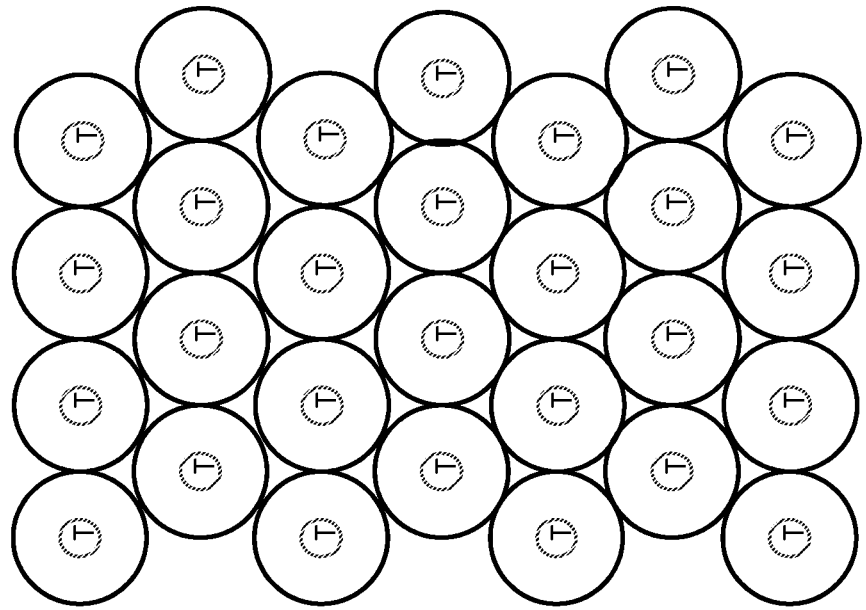
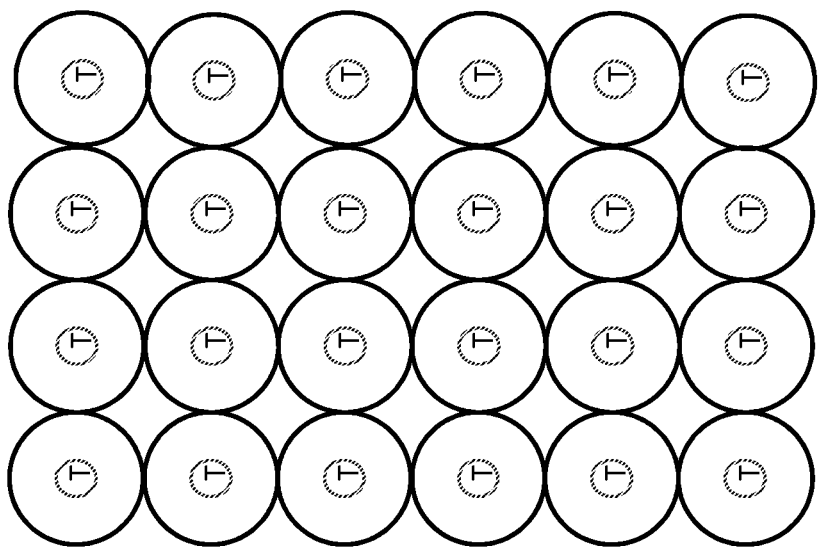
3 PHASE OPTION
28 TEMPERATURE SENSORS
2 PHASE OPTION
24 TEMPERATURE SENSORS
TEMPERATURE SIMULTANEOUS MEASUREMENTS
Fig 28B

APPARATUS AND METHOD FOR TREATING BIOLOGICAL TISSUE

CROSS-REFERENCE TO RELATED APPLICATIONS

This patent application claims the benefit of U.S. Provisional Patent Application No. 62/168,875 filed on May 31, 2015, which is incorporated herein by reference in its entirety.

BACKGROUND

The following issued United States patents and Unites States patent publications provide potentially relevant background material, and are all incorporated by reference in their entirety: U.S. Pat. Nos. 5,660,836, 5,873,849, 6,662,054, 6,662,054, 7,014,639, 8,014,878, 8,014,878, 8,172,835, 8,211,097, 8,813,756, 9,314,293, US 20030187488, US 20060259112, US 20070179482, US 20070239075, US 20100016849, US 20100160782, US 20100198199, US 20120226214, US 20120239120, US 20120310311, US 20130053929, US 20130137918, US 20130226269, US 20130245727, US 20130282085, US 20130331914, US 2013178764, US 20140213844, US 20140249609, US 20150088224, US 20160129273, US 20160129274, US 20160121112, U.S. Pat. No. 6,662,054, US 20160129274, US 20160121135 US20160129273, US20160129279. U.S. Pat. No. 8,014,878, US20160136462, US20160129274

SUMMARY OF EMBODIMENTS

Embodiments of the invention relate to a wearable device for delivering energy to biological tissue.

In different embodiments, the invention may relate to one or more of (i) methods and apparatuses for medical and/or aesthetic treatment (ii) a therapeutic wearable sleeve device for self-contained treatments, (iii) responding to biological feedbacks, (iii) noninvasive with robotic autonomous functional Skin interaction, fully independent and does not need a direct operator during treatments.

Apparatuses described herein can be self-contained, lightweight—for example, having the form factor of a wearable sleeve.

In some non-limiting examples, apparatuses described herein may comprise at least three components: (i) a Main Unit that includes the main control and/or houses a user interface (e.g. GUI) and/or some or all of modular drivers (e.g. that will be described later), (ii) the safety wearable control that, for example, allows the user to pause or stop the delivery of energy from the apparatuses, and (iii) a sleeve applicator part.

Applications include but are not limited to (i) warming treatment of sport injuries (ii) pain relief; (iii) loose and/or electrical muscles stimulation (e.g. to strength improve overall body strength) (iv) for use in cases of mild to moderate fat reduction (v) skin tightening (vi) corrective forming body contouring therapy (vii) cellulite reduction treatments.

The therapy may be based on multi-technology delivery—e.g. delivered simultaneously or sequentially (e.g. according to a predefined sequential procedure that depends on the real time monitoring of bio feedback parameters.

Some embodiments relate to use of radiofrequency multi channels and multiphase with Laser Lipolysis at the same time will have the Efficacy of combined Skin Tightening and Fat Reduction.

Some embodiments relate to the use of EMS/TENS pulses between the Radiofrequency predefined sequential procedure of pulse trains allow the use of the same Electrodes for both treatments.

Use of EMS/TENS pulse may improve circulation of lymph fluid.

Some embodiments relate to the optional use of PEMT—Pulsed Electro Magnetic Therapy, is for broken Bones Wound Therapy, Pain Relief.

Some embodiments relate to the option to add Vibration to the Applicator—for example, to help in the case of Increases metabolism of fat cells and/or to improves skin texture, and/or to increase skin elasticity and/or to stimulates lymphatic and blood circulation Different embodiments of the invention include one or more of the following features (i.e. any combination of the features below (or portions thereof) are within the scope of embodiments of the invention:

BRIEF DESCRIPTION OF THE DRAWINGS

FIG. 9 is an example of 2D array/chain of basic units.

FIG. 27A-27J relate to embodiments where a plurality of basic units are connected together (e.g. in a two-dimensional array of units—for example, addressable).

FIG. 28B describes a method of temperature simultaneous measurements from the whole treatment area for 2 phase and/or 3 phase sleeve applicators

DETAILED DESCRIPTION OF EMBODIMENTS

The claims below will be better understood by referring to the present detailed description of example embodiments with reference to the figures. The description, embodiments and figures are not to be taken as limiting the scope of the claims. It should be understood that not every feature of the presently disclosed methods, apparatuses, and computer readable media having stored thereon computer code for treating biological tissue is necessary in every implementation. It should also be understood that throughout this disclosure, where a process or method is shown or described, the steps of the method may be performed in any order or simultaneously, unless it is clear from the context that one step depends on another being performed first. As used throughout this application, the word "may" is used in a permissive sense (i.e., meaning "having the potential to"), rather than the mandatory sense (i.e. meaning "must").

Figure 1:
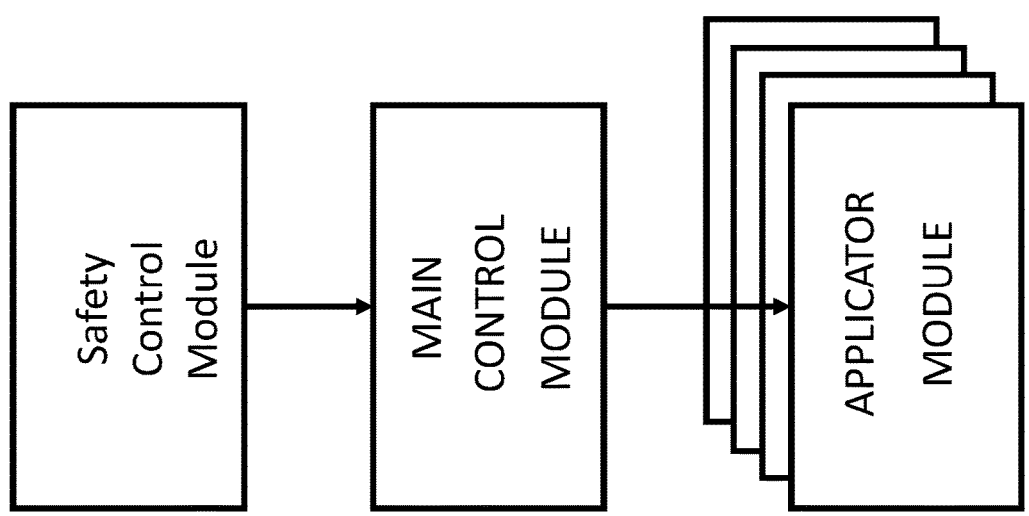
FIGS. 1-6 are block diagrams of systems and apparatus according to some embodiments of the invention.

Idea A In some embodiments, and as illustrated in FIG. 1, the Apparatuses described herein is divided to three major parts (not every part is required): the Main Unit that includes the main Control and the GUI and all the modular drivers that will be described later, the Safety wearable control that allow the user to STOP the delivery of Energy from the Apparatuses, and the new Inventive Applicator part that is the center part of this invention.

Idea B In some embodiments, Methods and Apparatuses for Medical and Aesthetics Therapeutic Wearable Sleeve device for self-contained treatments predefined and depend on biological feedbacks, Noninvasive with Robotic Autonomous functional Skin Interaction, fully independent Robotic, does not need a direct operator during treatment. Based on the Predefined parameters and the Biofeedback the Main Control start to deliver the Treatment Energy on all over the aria of the Wearable Applicator in a self-contained procedure so it cover all area in uniform circulation and keep the skin temperature in a steady level under the allowed threshold, Idea C In some embodiments, The Main Control Algorithm cause the Energy delivery to be adaptive, so it can be change during the area sequential procedure pass and even skip over parts of it depend on the local Temperature feedback, it will stop the Treatment in case of safety detection or predefined end of procedure.

Idea D In some embodiments, The Main Control RF delivery Algorithm works at nonlinear area pass, it jumps from one local area part to other local area part while jumping over the neighbor area part, in this way the all skin area heating under the Applicator become uniformity heated to the target temperature, the Diode Lipolysis LLLT (Low Level Laser Therapy) works during all of the treatment time.

Idea E In some embodiments, apparatuses described herein can be self-contained, lightweight, and wearable.

Idea F In some embodiments, For use in case of Warming Sport Injury the use of EMS/TENS pulses between the RF predefined sequential procedure of pulse trains allow the use of the same Electrodes for both treatments, the Diode Lipolysis LLLT (Low Level Laser Therapy) works during all of the treatment time Idea G In some embodiments, For use in case of Pain Relief the use of EMS/TENS pulses between the RF predefined sequential procedure of pulse trains allow the use of the same Electrodes for both treatments, the Diode Lipolysis LLLT (Low Level Laser Therapy) works during all of the treatment time Idea H In some embodiments, For use in case of loose and/or electrical Muscles Stimulation overall body the use of EMS/TENS pulses between the RF predefined sequential procedure of pulse trains allow the use of the same Electrodes for both treatments For example the rectus obdominis, the external oblique, the internal oblique and the trans versusabdominis.

Idea I In some embodiments, For use in case of mild to moderate Fat Reduction, the Diode Lipolysis LLLT (Low Level Laser Therapy) with multiphase RF will be used The use of Radiofrequency and Laser Lipolysis at the same time will have the Efficacy of combined Skin Tightening and Fat Reduction The use of EMS/TENS pulses between the RF predefined sequential procedure of pulse trains allow the use of the same Electrodes for both treatments Idea J In some embodiments, For use in case of Skin Tightening, the Diode Lipolysis LLLT (Low Level Laser Therapy) with multiphase RF will be used The use of Radiofrequency and Laser Lipolysis at the same time will have the Efficacy of combined Skin Tightening and Fat Reduction The use of EMS/TENS pulses between the RF predefined sequential procedure of pulse trains allow the use of the same Electrodes for both treatments Idea K In some embodiments, For use in case of Corrective Forming body contouring therapy Diode Lipolysis LLLT (Low Level Laser Therapy) with multiphase RF will be used The use of Radiofrequency and Laser Lipolysis at the same time will have the Efficacy of combined Skin Tightening and Fat Reduction The use of EMS/TENS pulses between the RF predefined sequential procedure of pulse trains allow the use of the same Electrodes for both treatments Idea L In some embodiments, For use in case of Cellulite Reduction Treatments Diode Lipolysis LLLT (Low Level Laser Therapy) with multiphase RF will be used The use of Radiofrequency and Laser Lipolysis at the same time will have the Efficacy of combined Skin Tightening and Fat Reduction Idea M In some embodiments, The Therapy based on multi technologic delivery at the same time or in a predefined sequential procedure that depends on the Real Time Monitoring Bio Feedback parameters.

Idea N In some embodiments, The safe control for effective Treatment, will be causing by biological feedbacks from the treatment area or by user control that placed on the safe wearable Sleeve unit on the user Arm, and will give the user the option to change the Treatment Level up or down or Stop the Energy delivery.

Idea O In some embodiments, The use of Radiofrequency and Laser Lipolysis at the same time will have the Efficacy of combined Skin Tightening and Fat Reduction.

Idea P In some embodiments, The use of EMS/TENS pulses between the RF predefined sequential procedure of pulse trains allow the use of the same Electrodes for both treatments Idea Q In some embodiments, The intend of use will be in Medical Centers and in comfortable and relaxing Fitness room, sports activity Centers or Spa-like environment, provide a body contouring apparatus employed in cosmetic body contouring treatments such as, but not limited to, fat reduction, body circumference reduction, cellulite reduction, skin tightening and skin rejuvenation at a clinical or dedicated professional setting Idea Q In some embodiments, use of PEMT—Pulsed Electro Magnetic Therapy, is for broken Bones wound Therapy, Pain Relief using unipolar Magnetic pulses up to 30 Hz, and for Pain case FIG. 1 is general block diagram including (i) a safety control Unit (ii) a main module (e.g. having the form factor of a wearable knapsack or having a table top or suitcase form factor); and (iii) an applicator module (e.g. sleeve applicator module). For example, the applicator module comprises at least one or at least two applications—e.g. operating in parallel.

FIG. 1 illustrates three modules (not all of which are required) including (i) an applicator module (e.g. a sleeve and/or a portion thereof and/or a sheet (e.g. flat or curved sheet—e.g. flexible sheet)) comprising an array (e.g. 2-D array)) of electrode (e.g. having rounded ends); (ii) a control module (e.g. including circuitry for addressing electrodes) and (iii) an optional safety module—e.g. including a 'stop switch'. For example, the main control unit may have a 'suitcase' form factor—see, e.g. FIG. 26.

Figure 2:
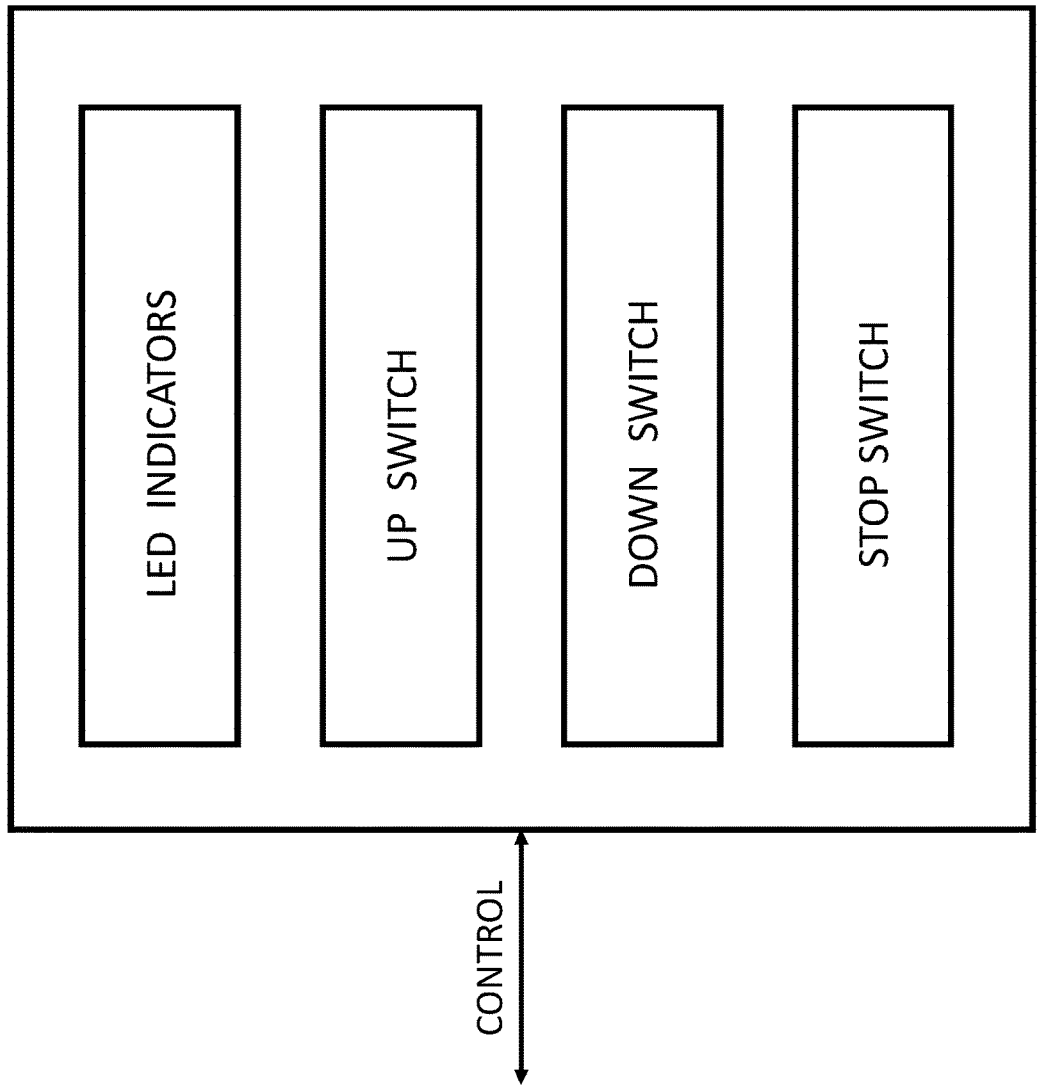
Figure 25:
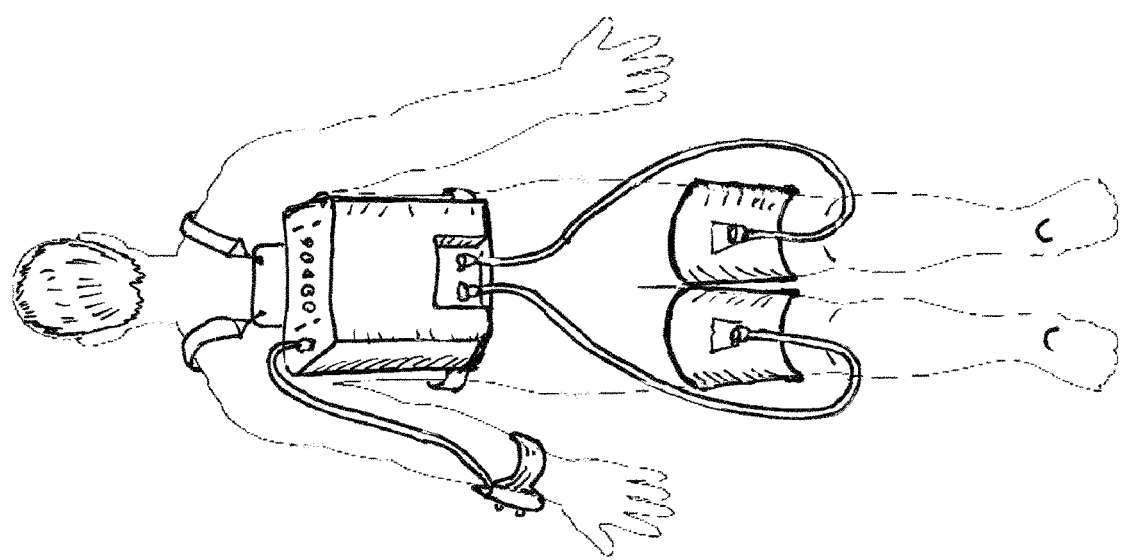

FIG. 2 illustrates a schematic block diagram of optional safety module including a switch—see also FIG. 25. In this case the user can stop treatment by engaging the 'safeswitch'

FIG. 2 is a block diagram of a safety control module (e.g. for a sleeve that is wearable on an arm). The safety control module comprises: (i) User Controls such as an UP and/or DOWN switches for raising or lowering an intensity of delivery energy; (ii) indicator(s) (e.g. LED indicators) and/or an optional LCD; and (iii) a 'STOP' switch—e.g. a panic button that allows the user to stop the system at any time and to summon the operator.

Figure 3:
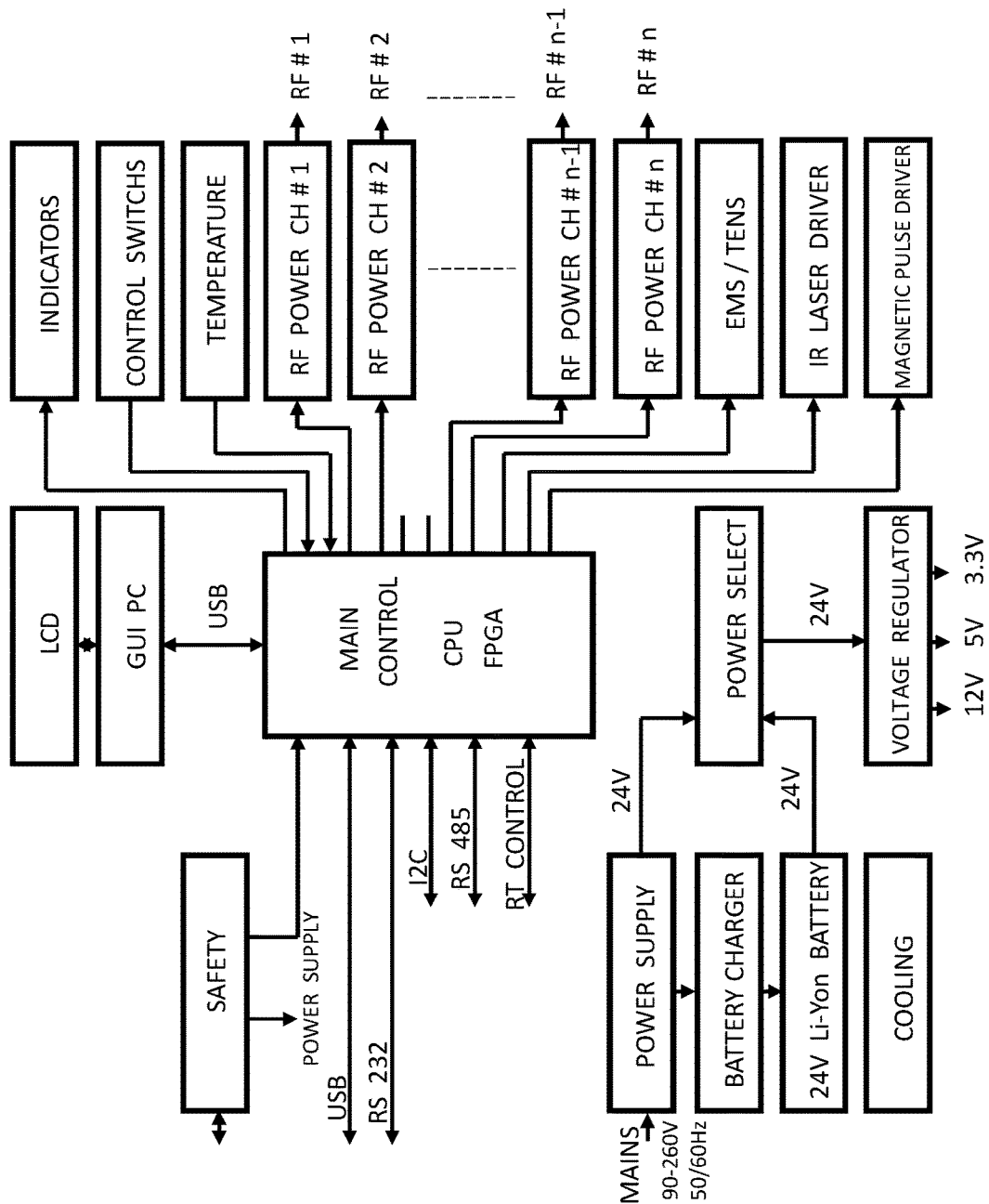
Figure 4:
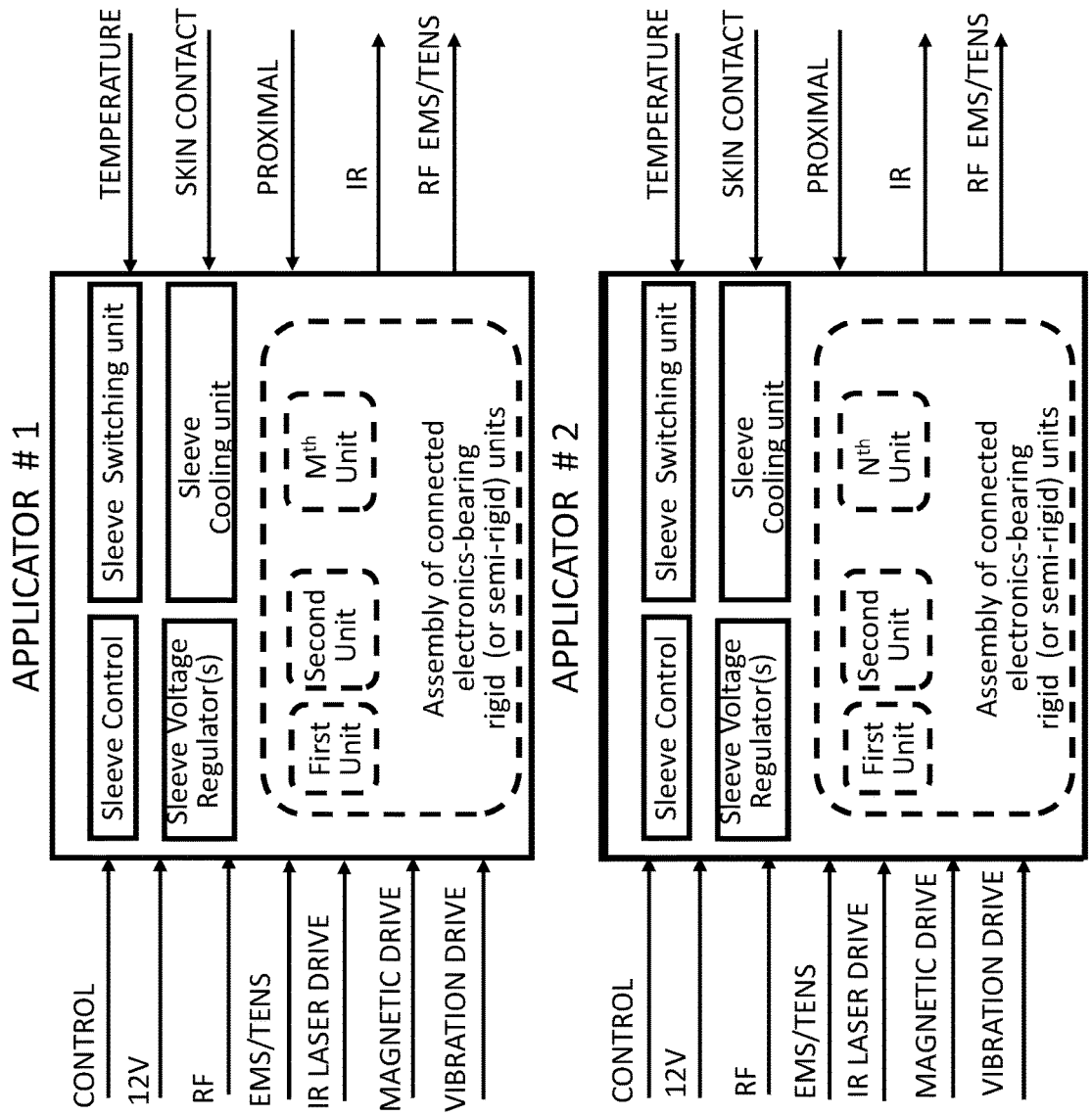

FIG. 3 is a block diagram of various elements of an energy delivery device. As shown in FIG. 4, in some embodiments, the device includes multiple applicators.

FIG. 3 is a block diagram of the main control unit (e.g. having any form factor—e.g. as a table top unit or as a knapsack). For example, the block diagram includes: (ii) GUI PC and LCD display module; (ii) Main Control Unit include FPGA and Safety interface module (iii) Multichannel and Multiphase Variable Radiofrequency drive for # n modules (iv) Power Radiofrequency Modules×n (Sine waves) (v) EMS/TENS Muscle stimulation and Nerve stimulation module (vi) Soft Leasers Diode for Lipolysis, multichannel drive module (in visible and Near-IR and IR wave longs) (vii) Ultrasound drive module (Optional) (vii) PEMT—Pulsed Electro Magnetic Therapy stimulation drive module (Optional) (viii) Cooling drive and FAN module and (ix) Real Time Monitoring Bio Feedback parameters (x) System Health Monitoring, Voltage, Currents, Temperature, Diagnostics (xi) Medical Isolation barrier for 4 KV (Optocouplers, Isolated DC/DC) (xii) Medical universal Power supply module (xiii) Battery Charger Module for the Wearable Knapsack option (xiv) Power Source from rechargeable Batteries or Universal Mains. The skilled artisan will appreciate that not every element is required.

FIG. 4 is a block diagram of a wearable applicator (e.g. having a sleeve form-factor). Once again, not every element is required. In the example of FIG. 4, two sleeve applicators (e.g. two sleeves—e.g. one worn on each arm) are illustrated. The sleeve applicators may work simultaneously—e.g. controlled by common control unit (NOT SHOWN).

Figure 8A:
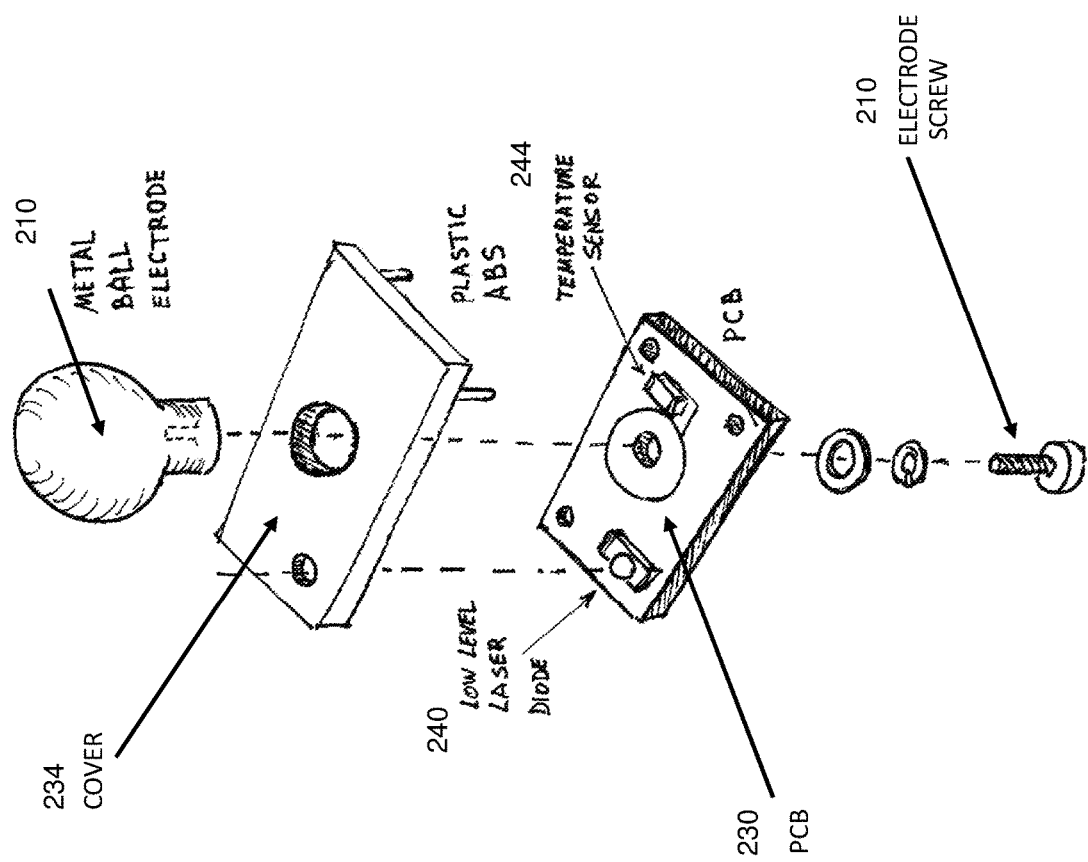
FIGS. 8A-8B each illustrate a non-limiting example of a single basic unit.
Figure 8B:
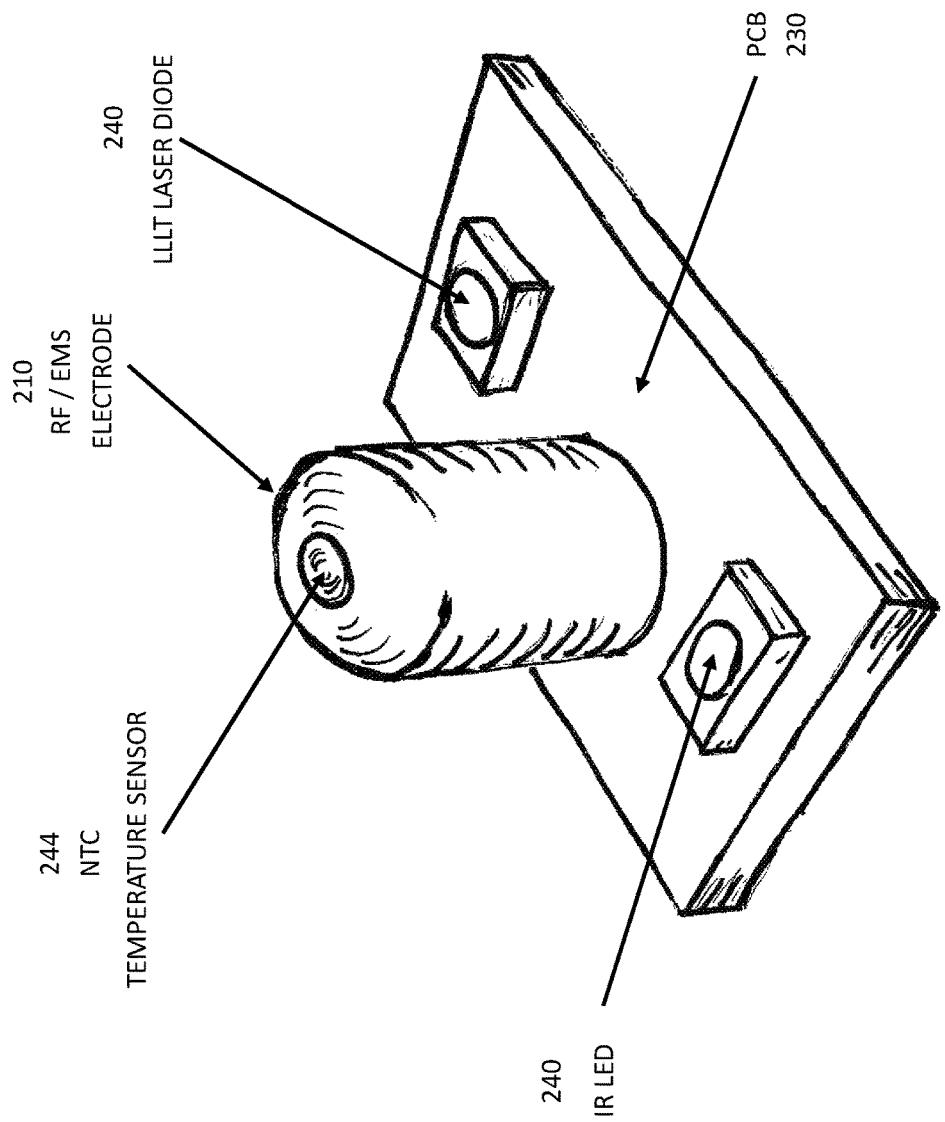

In the illustrated example of FIG. 4, each applicator comprises a plurality of rigid or semi-rigid units—for example, each basic (e.g. rigid or semi-rigid) unit providing one or more features of FIG. 8A and/or FIG. 8B. Furthermore, the rigid or semi-rigid units may be linked to each other to provide a 'mail'-like form factor—for example, as shown in FIG. 9. Each basic (rigid or semi-rigid) unit may include an elastic and/or nonmetal portion Each rigid or semi-rigid unit may further include one or more of: (i) unit-local electrode for RF and/or EMS/TENS and/or (ii) Electronics PCB Switching circuit; and (iii) laser diode for Lipolysis and Temperature Sensor.

Furthermore, each sleeve applicator may include one or more of: (i) a sleeve-local controller (e.g. comprising central applicator control board), (ii) a sleeve-local switching unit (e.g. switching matrix to regulating addressing and specification of unit(s) to which is electrical energy is delivery, one or more sleeve-locator regulator(s) (e.g. voltage-regulator(s)), and (iii) a cooling unit (comprising a fan). In some embodiments, each sleeve applicator comprises one or more of: LED Indicators Optional AIR Coil for the Magnetic PEMT, and Optional Vibration element.

Figure 5:
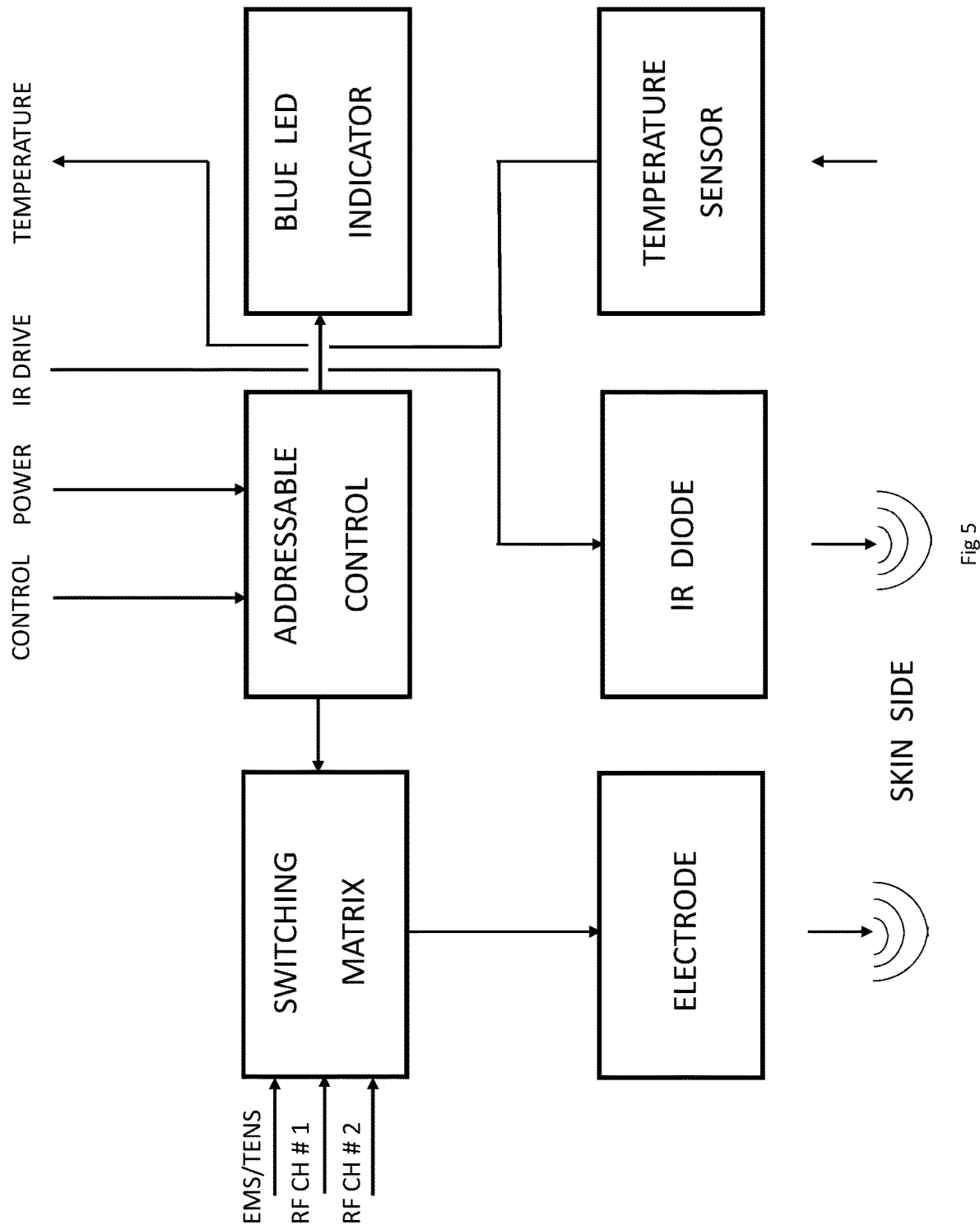

FIG. 5 relates to a single basic unit—for example, in FIG. 4 there are M basic units in the first applicator and N basic units in the second applicator where M and N are positive integers (e.g. each greater than 5 or each greater than 10 or each greater than 25 or each greater than 50). In the illustrated example of FIG. 5, each basic unit comprises an electrode (e.g. rounded such as metal-ball electrodes)—e.g. a basic-unit-specific switching matrix is addressable by an addressable control (e.g. according to its address) so as to selectively deliver power to the electrode. Each electrode, for example, may be attached to or mounted to a respective plate (e.g. electrically insulating plate and/or rigid and/or semi-rigid plate). In the particular example of FIG. 5, each basic unit includes an IR diode and/or a bleu LED indicator and/or a temperature sensor—e.g. for directly or directly sensing a temperature of biological tissue (e.g. at the epidermis and/or any depth therebeneath).

Figure 6:
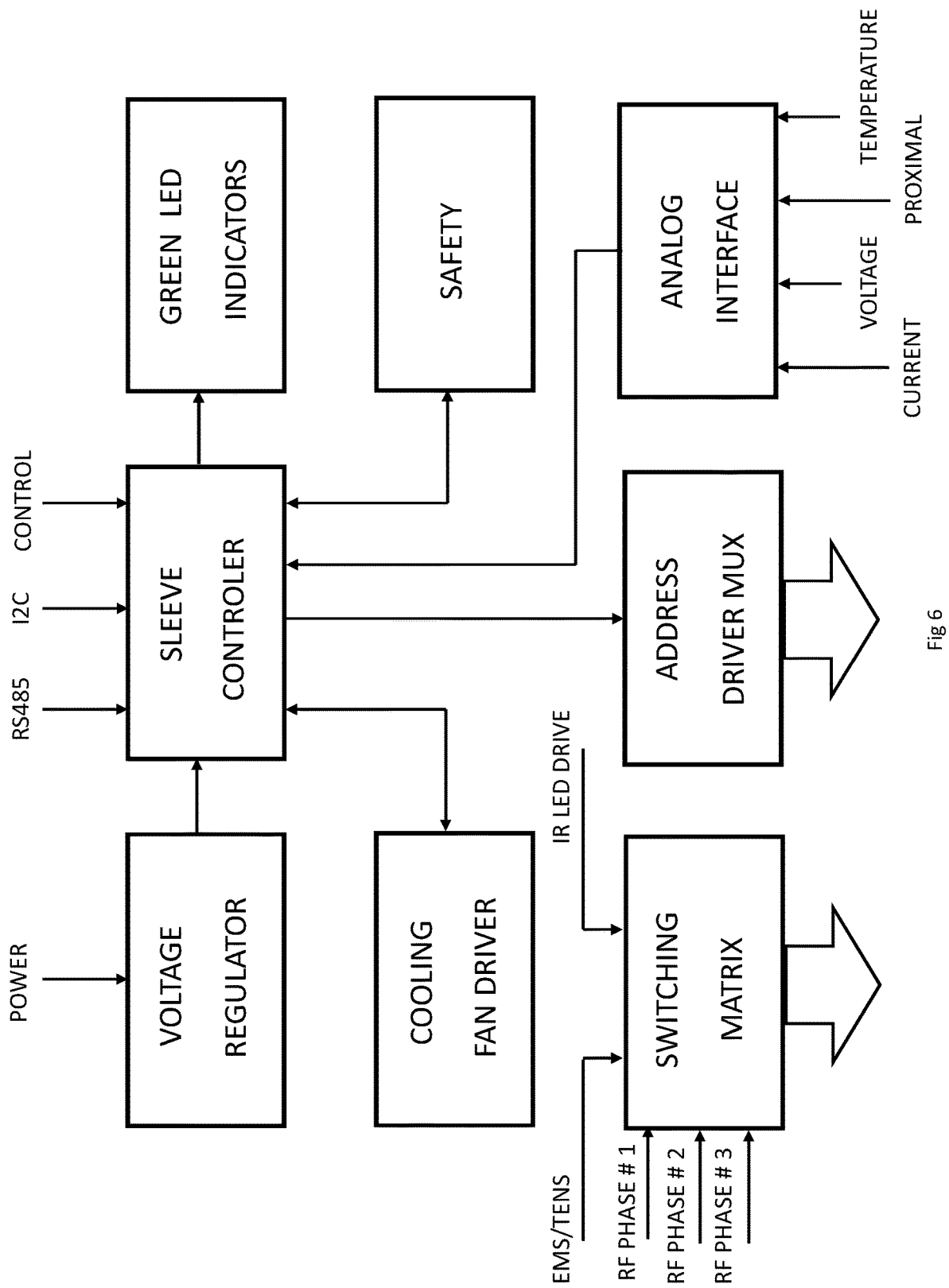

FIG. 6 illustrates one control diagram for a multi-basic-unit sleeve (e.g. wearable sleeve) comprising a plurality of basic units (e.g. see FIG. 5 as a block diagram of a single basic unit). In the example of FIG. 6, the multi-basic unit sleeve may include any combination of the following element: Sleeve Controller, Voltage Regulator, Indicators LED, FAN drive control, Main Switching Matrix, Address Mux driver, Analog Interface, and Safety circuits.

Figure 7:
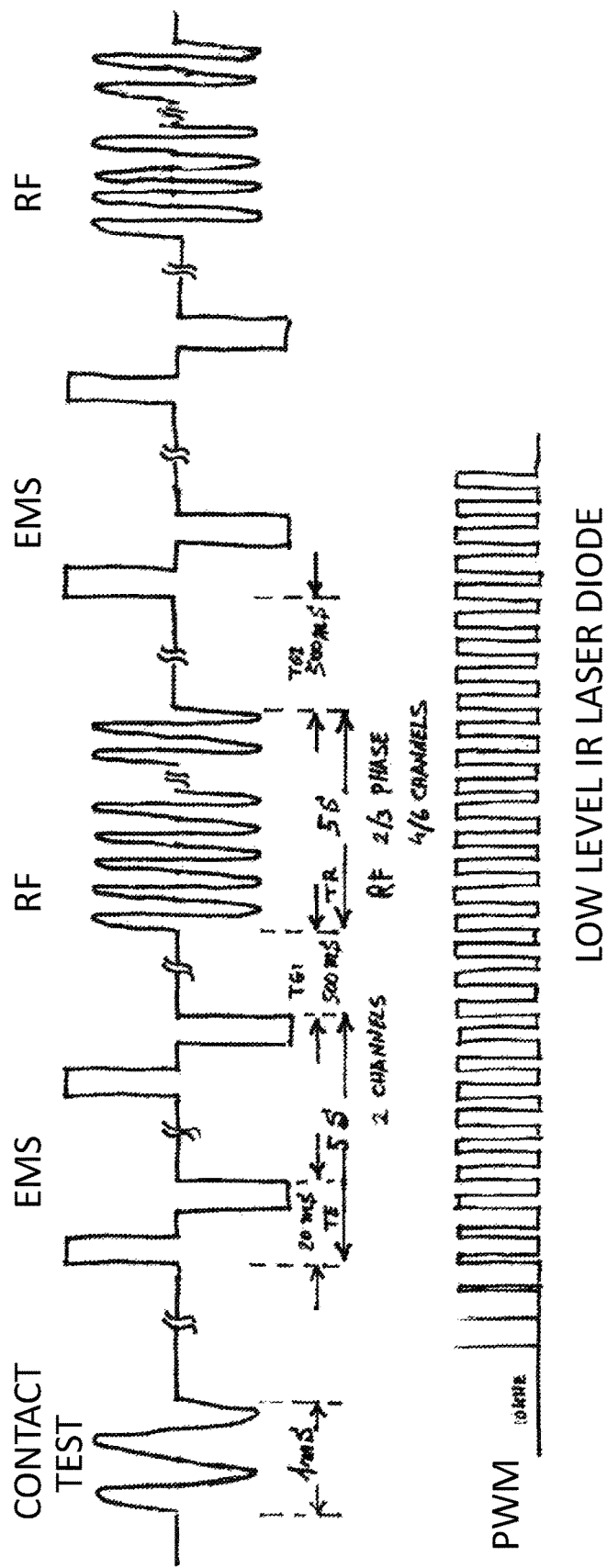
FIG. 7 illustrates waveform diagram.

FIG. 7 illustrates waveform diagram (e.g. not every type of energy is required—any combination may be provided). In FIG. 7, the Waveform Diagram includes: RF and/or EMS mixed with RF signal, Low Level Laser Diodes PWM signal, The Pulsed Electromagnetic Therapy—PEMT FIGS. 8A-8B each illustrate a non-limiting example of a single basic unit including a plate and an electrode (e.g. having a rounded end)—for example, deployed to a circuit board (e.g. PCB). Each plate may be flat or curved—e.g. concave facing toward the epidermis. In the example of FIG. 8A includes: a board of a basic unit (one of m×n units), an electrode (e.g. metal ball electrode), a plate constructed from an electrical insulator (e.g. plastic ABS), a PCB including a Laser LED and/or a Temperature Sensor (e.g. IR-based temperature sensor). In the example of FIG. 8A, the basic unit also includes a low level laser diode.

Reference is now made to FIG. 8B which is a diagram in another embodiment of a basic unit. In FIG. 8B, the basic unit comprises: (i) a temperature sensor integrated with the RF/EMS electrode (210 and 244) and (ii) the LLLT diodes (240) and PCB (230)

FIG. 9 is an example of 2D array/chain of basic units—e.g. for an abdominal sleeve.

Figure 27A:
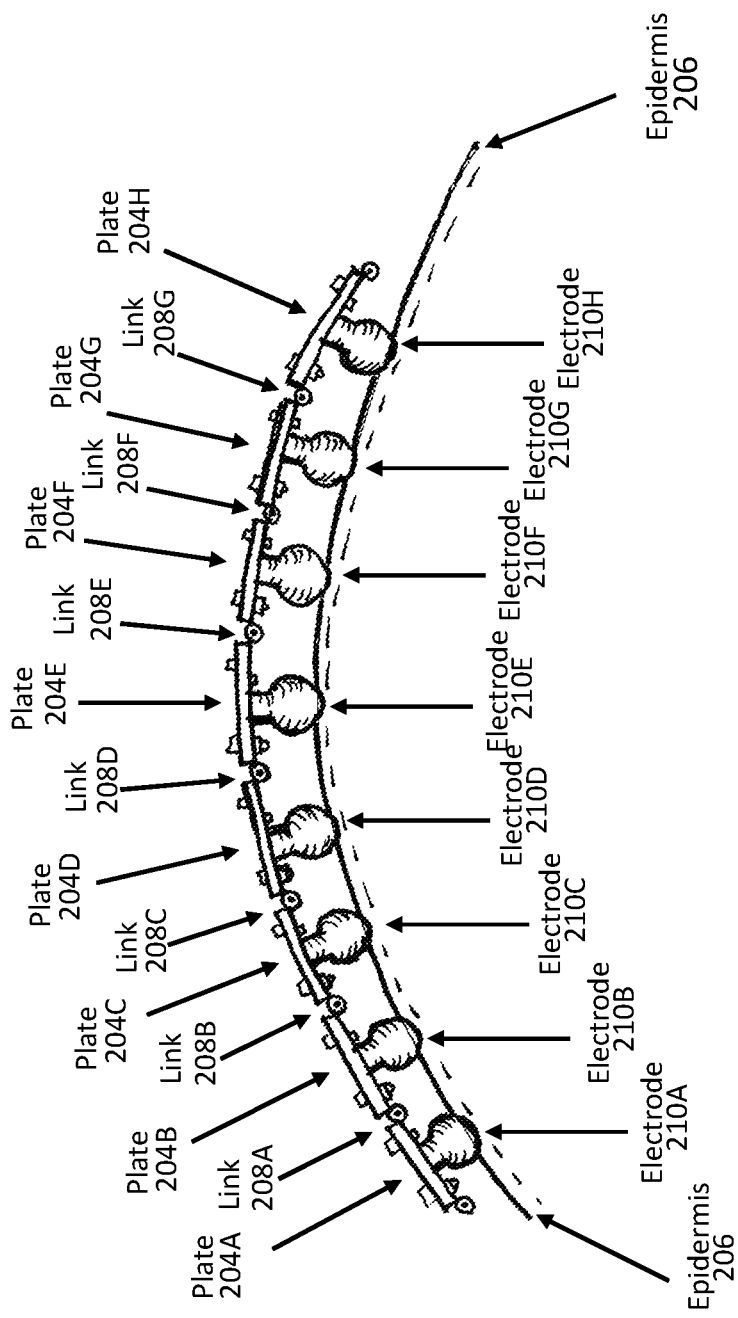

FIG. 27A is a side-view of an array (e.g. 2D array) of plate/board basic units including plates 204A-204H are connected together via links 208A-208G—for example, each basic unit includes a respective electrode—thus, FIG. 27A shows electrodes 210A-210H. In some embodiments, each plate is rigid and/or semi-rigid and/or malleable. Collectively, each electrode may face towards epidermis 206. In some embodiments, the flexibility of the 2D-array (e.g. flat or curved sheet and/or sleeve or portion thereof) exceeds the flexibility of each individual plate.

Thus, FIG. 27A illustrates details of basic chain boards, where each board has a PCB Plate Electrode for RF/EMS that will be in touch with the Epidermis 206. The Basic chain boards are connected each to other with a flex link (see 208A-208G).

Figure 27B:
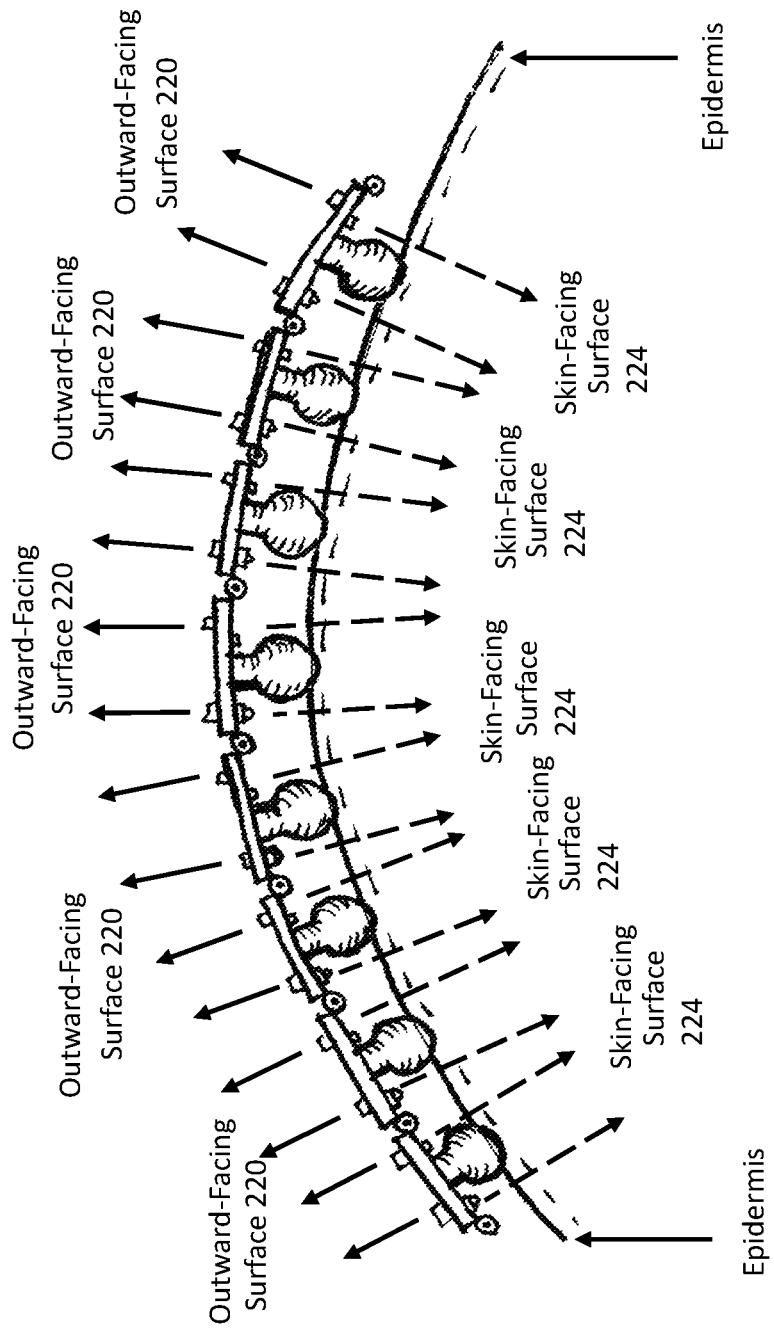

FIG. 27B illustrates the same array of FIG. 9—this illustrates outward-facing surface/side 220 and a skin-facing side/surface 224.

Figure 27C:
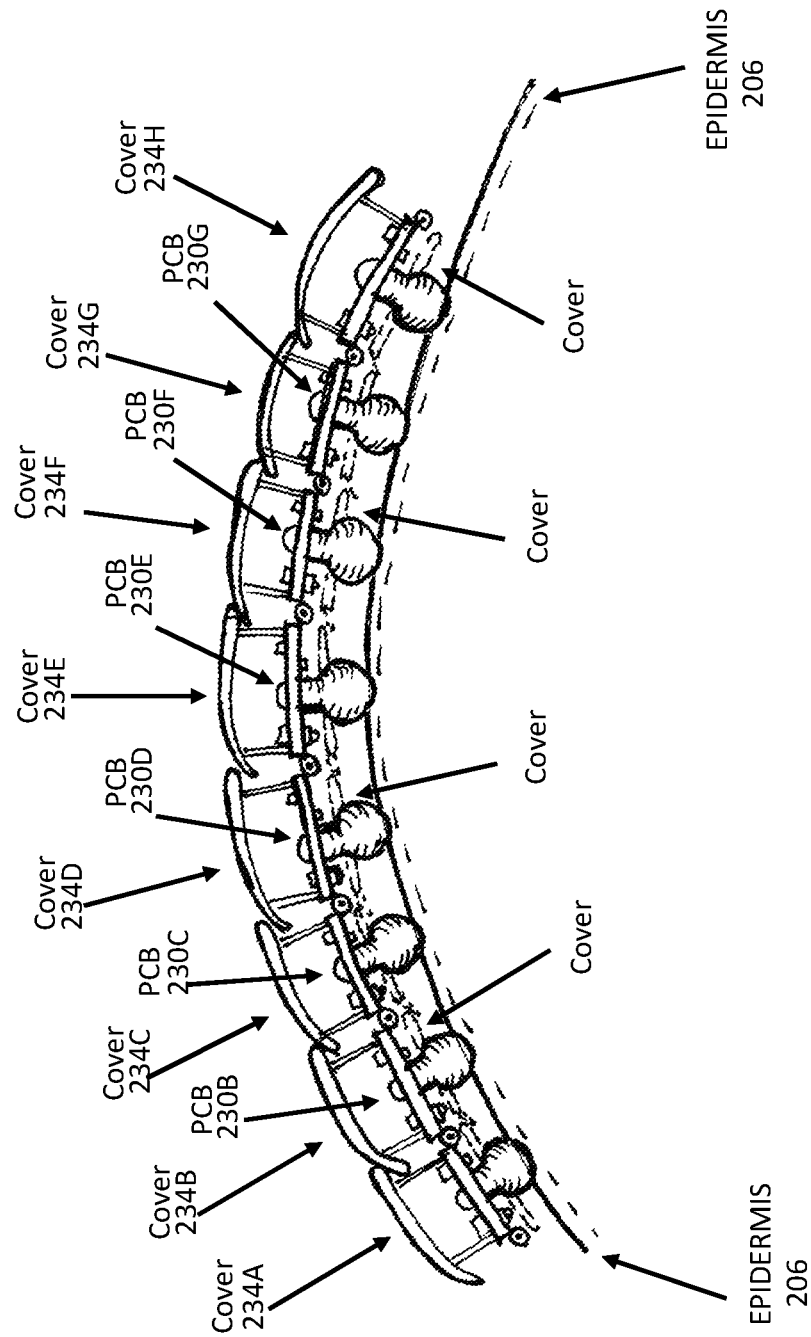

In some embodiments as shown in FIG. 27C, each plate is associated with a respective cover—e.g. the covers may overlap. Illustrated in FIG. 27C are covers 234A-234H which are respectively associated with PCB boards of the basic units—illustrated in FIG. 27C are PCB boards 230A-230G.

Figure 27D:
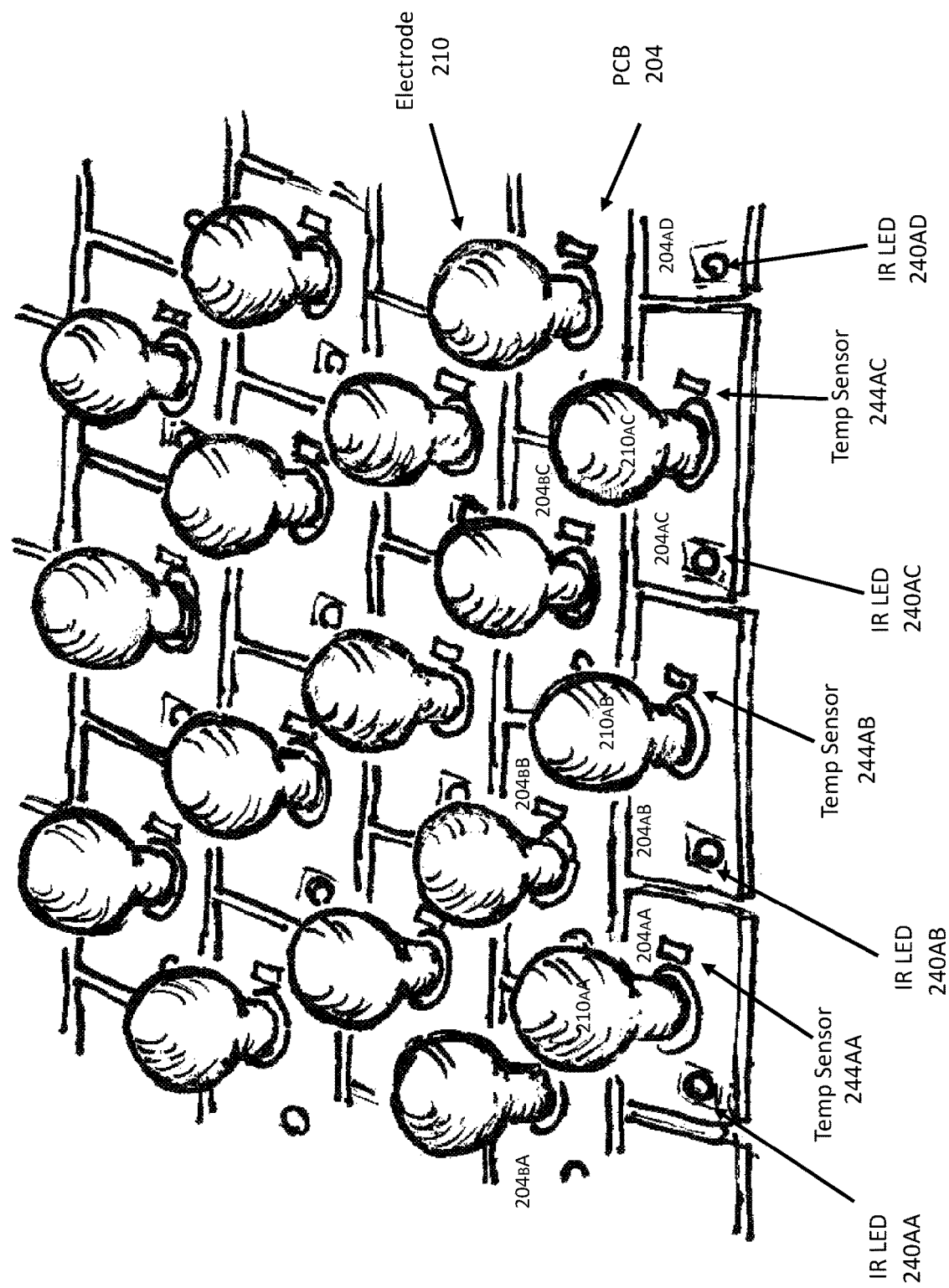

FIG. 27D is a top-view of the 2D array of plate units of FIG. 27A including LEDs (and/or laser diodes) and electrodes and temp. sensors (e.g. to directly or indirectly sense temperature). The Details of basic chain boards PCBs (204AA, 204AB, 204AC, 204AD, 204BA, 204BB, 204BC) has on its surface IR LED and LLLT LED/LASER diodes (240AA, 240AB, 240AC, 240AD), IR Temperature sensors (244AA, 244AB and 244AC), and the RF/EMS electrodes (210, 210AA, 210AB, and 210AC).

Figure 27E:
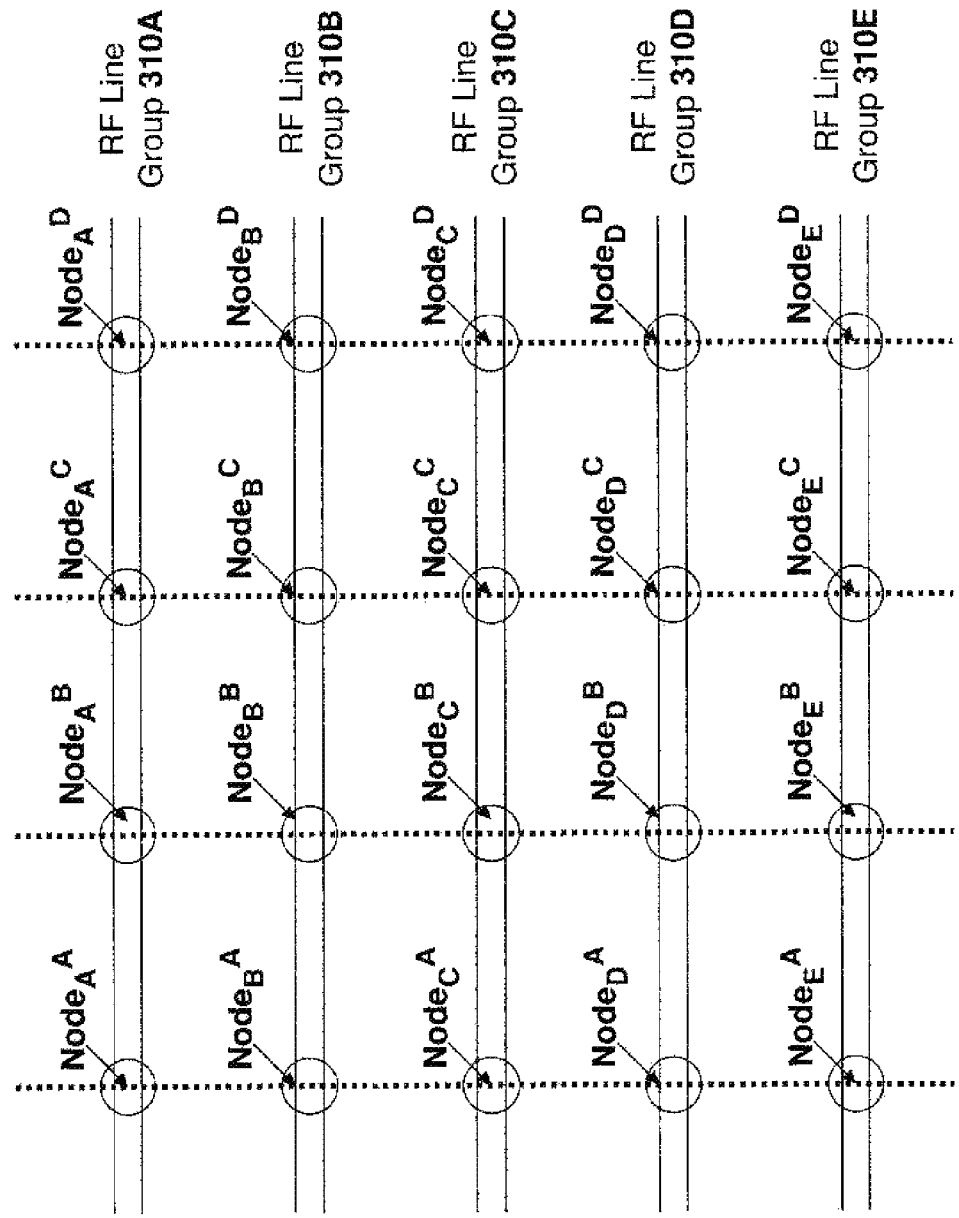
Figure 27F:
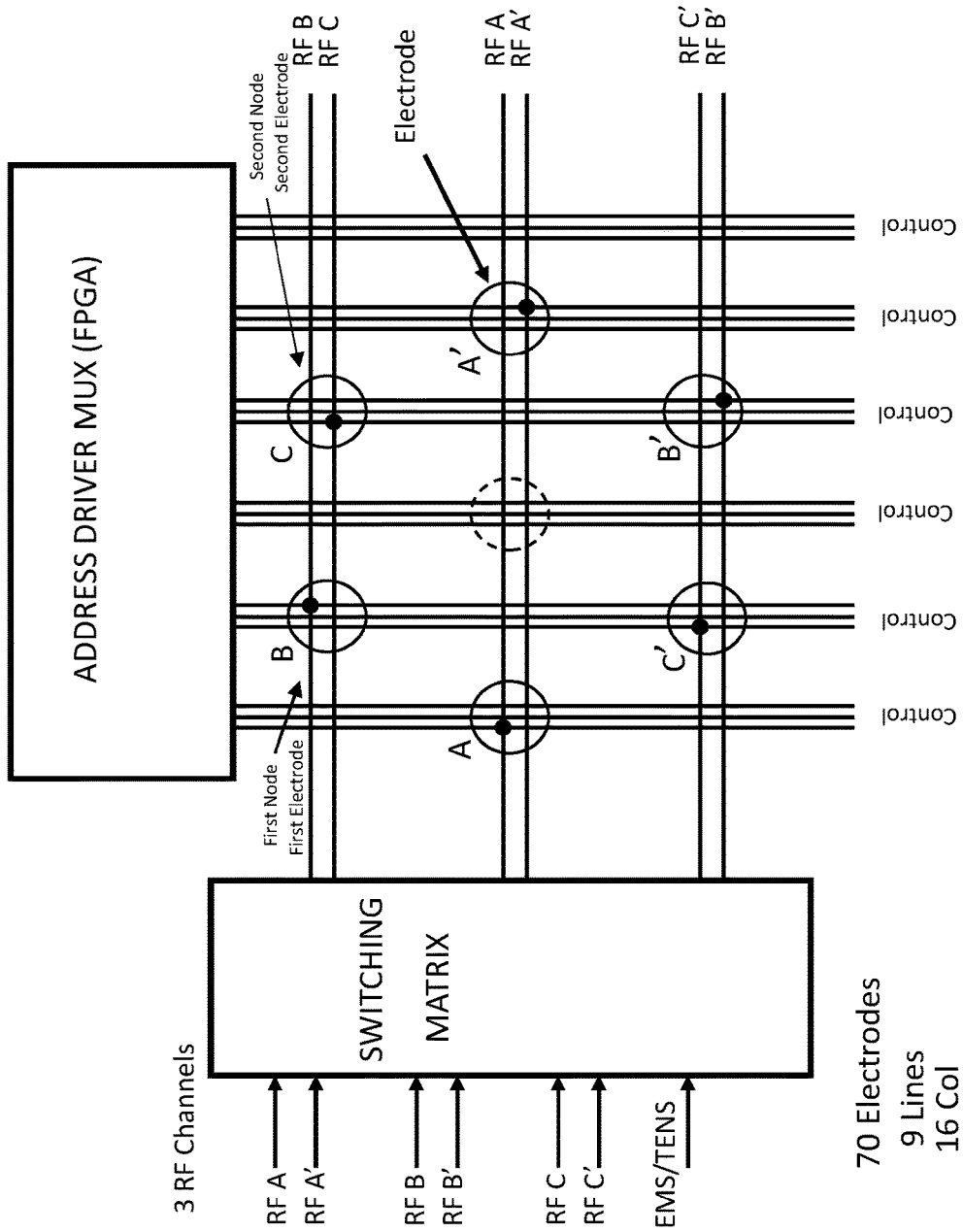

FIGS. 27E and 27F illustrates an RF node-matrix comprising:
i. plurality of parallel RF voltage lines (illustrated in FIGS. 27E and 27F as horizontal—each RF line group 310 comprises one or more or two or more or three or more parallel RF voltage lines);
ii. a plurality of control-signal lines (illustrated in FIGS. 27E and 27F as vertical—each control line may illustrate a one bit or two bit or three bit or >3 bit control signal), the RF voltage lines and control signal lines defining a two-dimensional array of control nodes (illustrated in FIG. 27E) such that two or more RF voltage lines pass through each control node, each RF electrodes of the plurality of RF electrodes being resident at a different respective control-node (each node as 1 or 2 or more switches—for the plurality of electrodes, each electrode is deployed at a node—there is no requirement that every nod host an electrode) iii. a plurality of switches (see the bottom right of FIG. 27F—this is one example where each node has 2 switches and is not a limitation), wherein each RF-electrode-hosting control-node includes a respective plurality of switches for specifying (A) if the electrode hosted at the control node is connected to one of the RF voltage lines passing through the control node (and (B) if so, which one of the RF voltage lines.

Shown in 27E are lines 310A-, 310B, 310C, 310D and 310E.

FIG. 27F shows the Details of Switching basic chain boards connections to switching matrix and to the address driver FPGA mux.

Also illustrated in FIG. 27F is: (i) d. an address driver MUX controller (see the top of FIG. 9F) for sending control signals via each of the control-signal lines to control the switches to specify for each RF-electrode-hosting-control node (A) if the electrode hosted at the control node is connected to one of the RF voltage lines passing through the control node and (B) if so, which one of the RF voltage lines.

Also illustrated in FIG. 27F (see left side) is e. a plurality of RF channels, each RF channel defining an RF signal having first and second poles—thus as shown in FIG. 9F there are 3 RF channels and one EMS channel; RF channels—a first channel defined by A and A'; a second channel defined by B and B'; a third channel defined by C and C'. A and A' may be 'pole and anti-pole'; B and B' may be 'pole and anti-pole'; and C and C' may be 'pole and anti-pole'—e.g. see 9J where the poles are offset by 120 degrees.

Each RF line (of the line groups 310A) may be connected either to none of the RF channels or to one of the switching channels. In the non-limiting example of FIG. 27F, the top pair of RF lines (corresponding to line group 310A) are connected respectively to (i) the 'pole' of the second RF channel (i.e. the 'B' signal); and (ii) the 'pole' of the third RF channel (i.e. the 'C' signal).

In the non-limiting example of FIG. 27F, the middle pair of RF lines (corresponding to line group 310B) are connected respectively to (i) the 'pole' of the first RF channel (i.e. the 'A' signal); and (ii) the 'anti-pole' of the first RF channel (i.e. the "A'" signal).

In the non-limiting example of FIG. 27F, the bottom pair of RF lines (corresponding to line group 310C) are connected respectively to (i) the 'anti-pole' of the third RF channel (i.e. the "C'" signal); and (ii) the 'anti-pole' of the second RF channel (i.e. the "B'" signal).

Thus, any channel of the plurality of RF channels (i.e. either the pole or the anti-pole) can be connected to any input of the switching matrix (i.e. each RF line has it's own respective input). This allows to control electrodes to selectively apply voltages to each electrode.

Thus, in FIG. 27F, the "first" electrode at the 'first node" is attached to the top line within line group 310A—this is because of the control signal via the address driver MUX which controls the switches resident at the 'first node.'.

In FIG. 27F, the "second" electrode at the 'second node" is attached to the bottom line within line group 310A—this is because of the control signal via the address driver MUX which controls the switches resident at the 'second node.'.

Figure 27G:
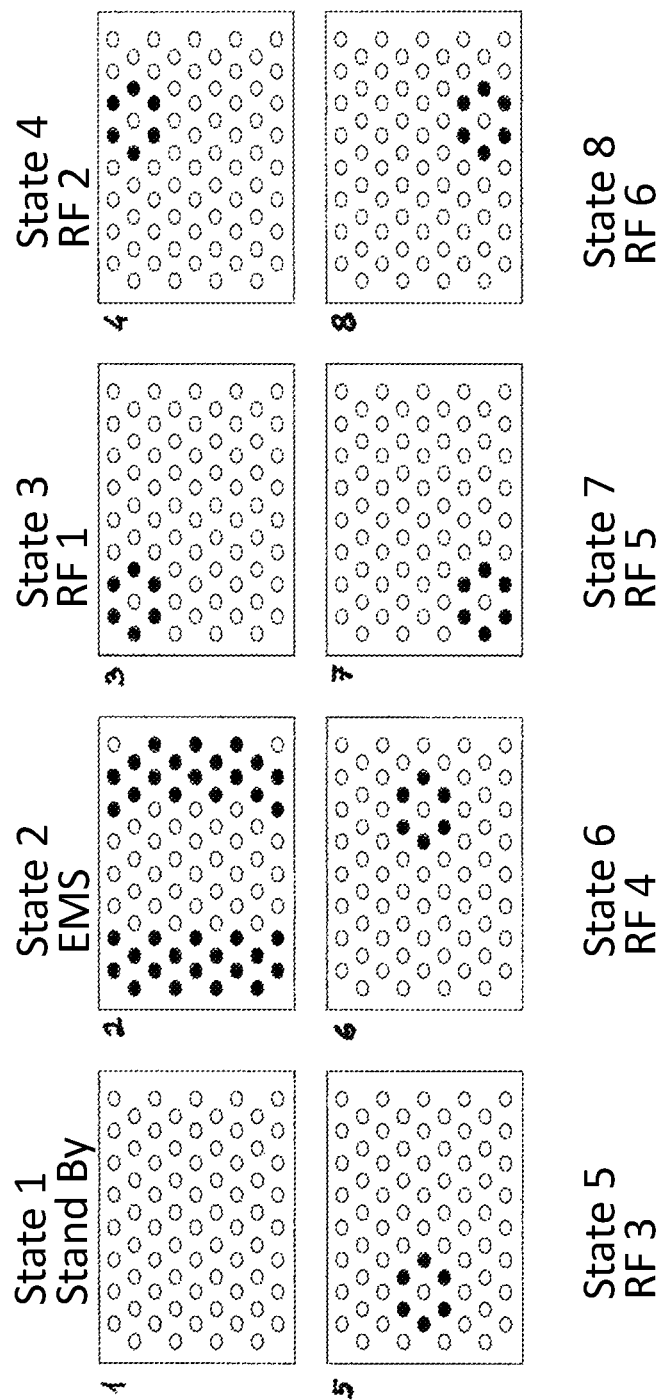

FIG. 27G illustrates a plurality of states of operating the 2D-array of electrodes of the energy-delivery device. In 'state 2' the electrodes on the left (column of 'darkened circles") are maintained as 'poles' (e.g. using the switching matrix and the address driver MUX) and the electrodes on the right (column of 'darkened circles") are maintained as 'anti-poles'—e.g the input to the 'switching matrix' are not RF includes as shown in FIG. 27F but rather EMS inputs (i.e. pole and anti-pole)—the switches provide the pattern illustrated in FIG. 27G state 2.

FIG. 27G illustrates 16 states—it is possible to control switching matrix and address MUX to sequentially transition the energy-delivery device through each states where each state represents an 'operation mode' for delivering RF and/or EMS energy. States 3-16 relate to delivery of RF energy.

FIG. 27G shows: (i) Operation State from 1 to State 8 with detail of each state (ii) The open sleeve Applicator, for example with 70 Electrodes, and (iii) 42 Treatment Areas, the optional sequence and the Treatment order with six active Electrodes, on each state(only the 16 first steps are shown).

The states are defined as follows: State #1 is for non active state; State #2 is for EMS Pulsing; State #3 is the RF on limited Area.

Figure 27H:
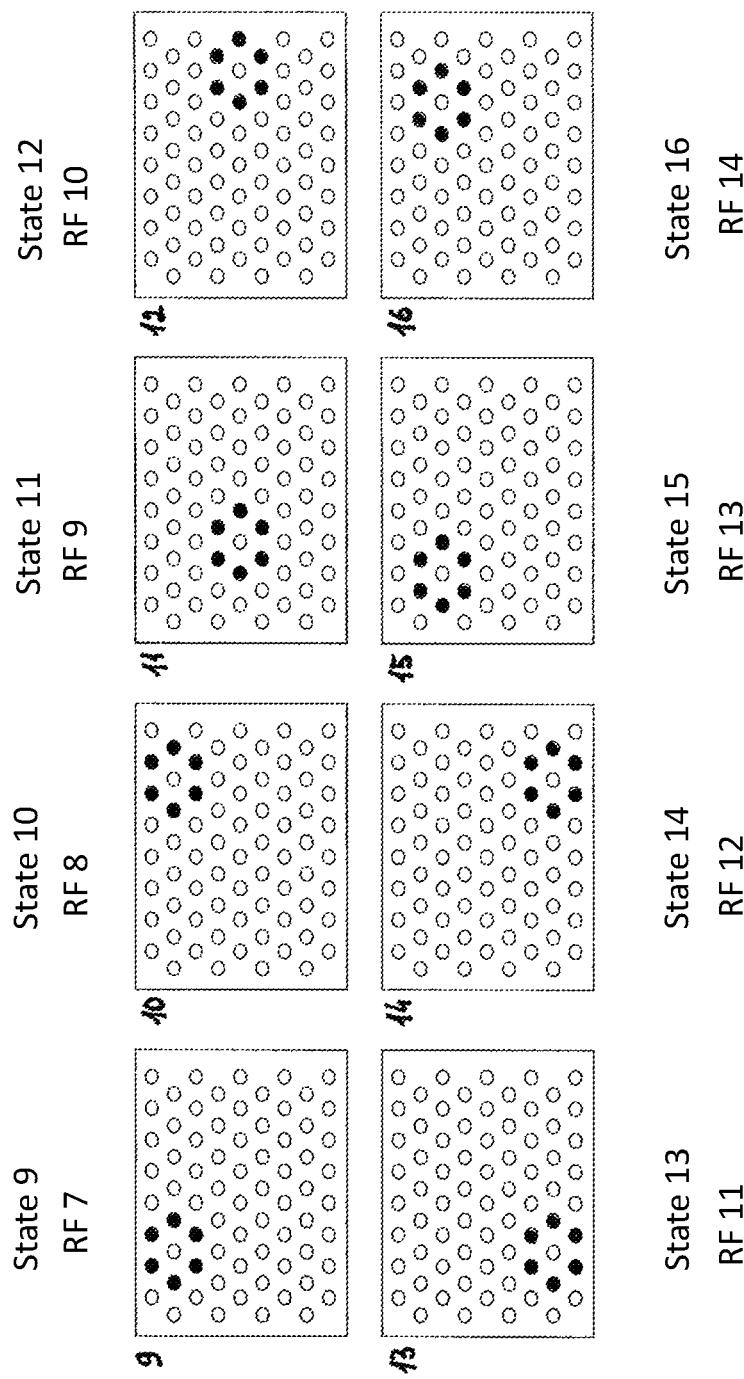

FIGS. 27H-27I relate to state 11.

FIG. 27H shows Operation State from 9 to State 16 with detail of each state

FIG. 27I Operation State 11 detailed electrode (210) state, phase A (0 degrees) connected between 210A and 210D, phase B (+120 degree) connected between 210B and 210E and phase C (+240 degree) connected between 210C and 210F, electrode 210G is disconnected.

Figure 27J:
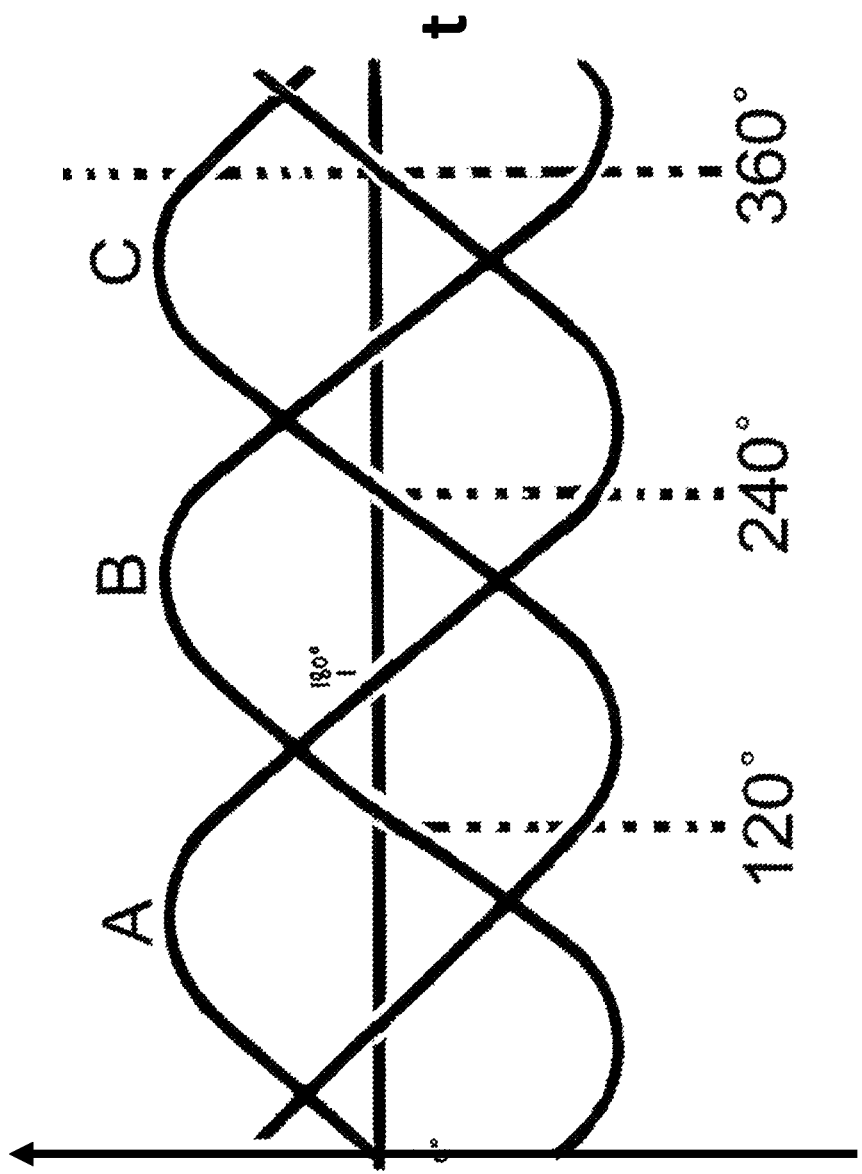

FIG. 27J: Operation 3 Phase Signal, phase A (0 degree), phase B (+120 degree), phase C (+240 degree).

As shown in FIG. 27I, it is possible to a 'passive electrode' (e.g. according to the switches not connected to any RF line) to be disposed in between Electrode 210G (e.g. passive in FIG. 27I according to the switches) may sometimes between passive (i.e. not connected to any RF line according to the switches) and sometimes be 'active' (e.g. connected to one of the RF lines). By providing this feature (i.e. where electrode may be passive an located in between one or more pole/anti-pole pair—in FIG. 27I, electrode 210G is passive and between three pole/anti-pole pair) and where the electrode may at other times (i.e. not illustrate in FIG. 27I) to be connected to one of the RF lines (i.e. according to the switch) so electrode 210G functions as a pole or anti-pole (mode NOT SHOWN).

As shown in FIG. 27J, it possible to operate in N phases where N=2 or 3 or 4 or any larger integer—FIGS. 27I-27J relate to the example N=3.

FIG. 27B shows The Details of basic chain boards, that skin facing surface to the Epidermis (224) and outward facing surface (220)

FIG. 27C shows The Details of basic chain boards PCB (230) that have a cover on the side facing surface to the Epidermis (206), and has a cover outward facing surface (234)

FIG. 27D shows The Details of basic chain boards PCB (204) has on it surface IR LED and LLLT LED/LASER diode (240), IR Temperature sensor (244), and the RF/EMS electrode (210)

FIG. 27E shows The Details of basic chain boards connection to the RF/EMS lines (310) and its addressable node placement FIG. 27F shows The Details of Switching basic chain boards connections to switching matrix and to the address driver FPGA mux FIG. 27G shows Operation State from 1 to State 8 with detail of each state The open sleeve Applicator, for example with 70 Electrodes, and 42 Treatment Areas, the optional sequence and the Treatment order with six active Electrodes, on each state. (Only the 16 first steps are shown).

State #1 is for non active state
State #2 is for EMS Pulsing
State #3 is the RF on limited Area FIG. 27H shows Operation State from 9 to State 16 with detail of each state FIG. 27I shows Operation State 11 detailed electrode (210) state, phase A (0 degree) connected between 210A and 210D, phase B (+120 degree) connected between 210B and 210E and phase C (+240 degree) connected between 210C and 210F, electrode 210G is disconnected FIG. 27J: Operation 3 Phase Signal, phase A (0 degree), phase B (+120 degree), phase C (+240 degree)

Figure 10:
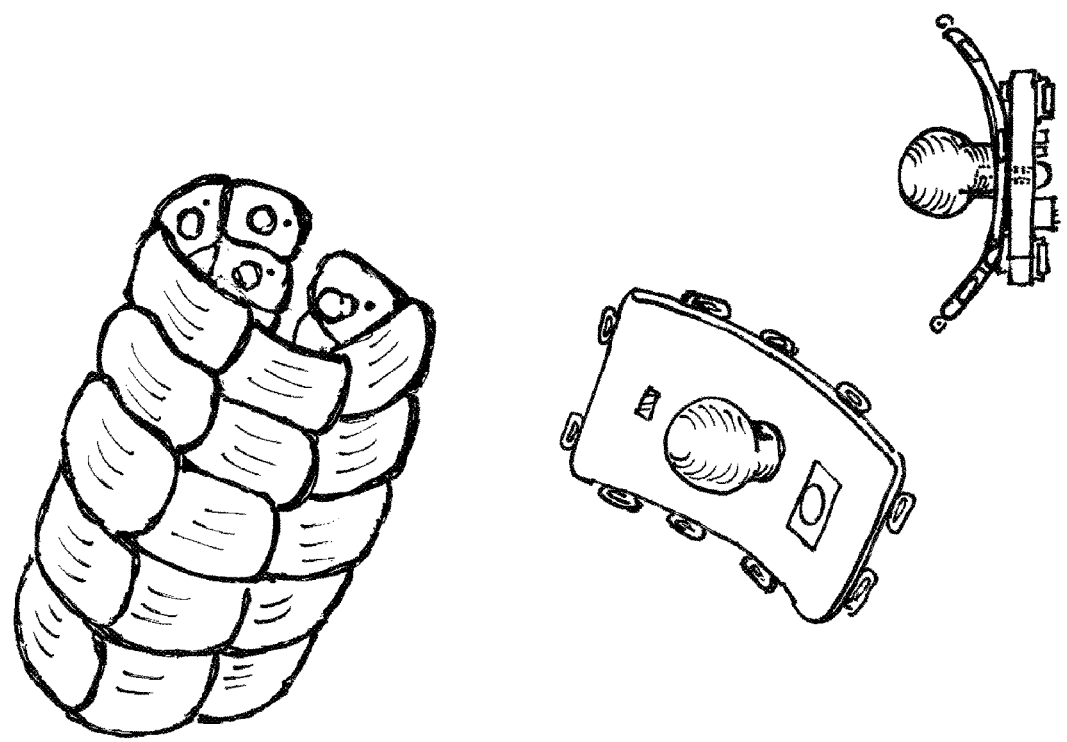
FIG. 10-12, 16-26 illustrate different form factors of a sleeve.
Figure 11:
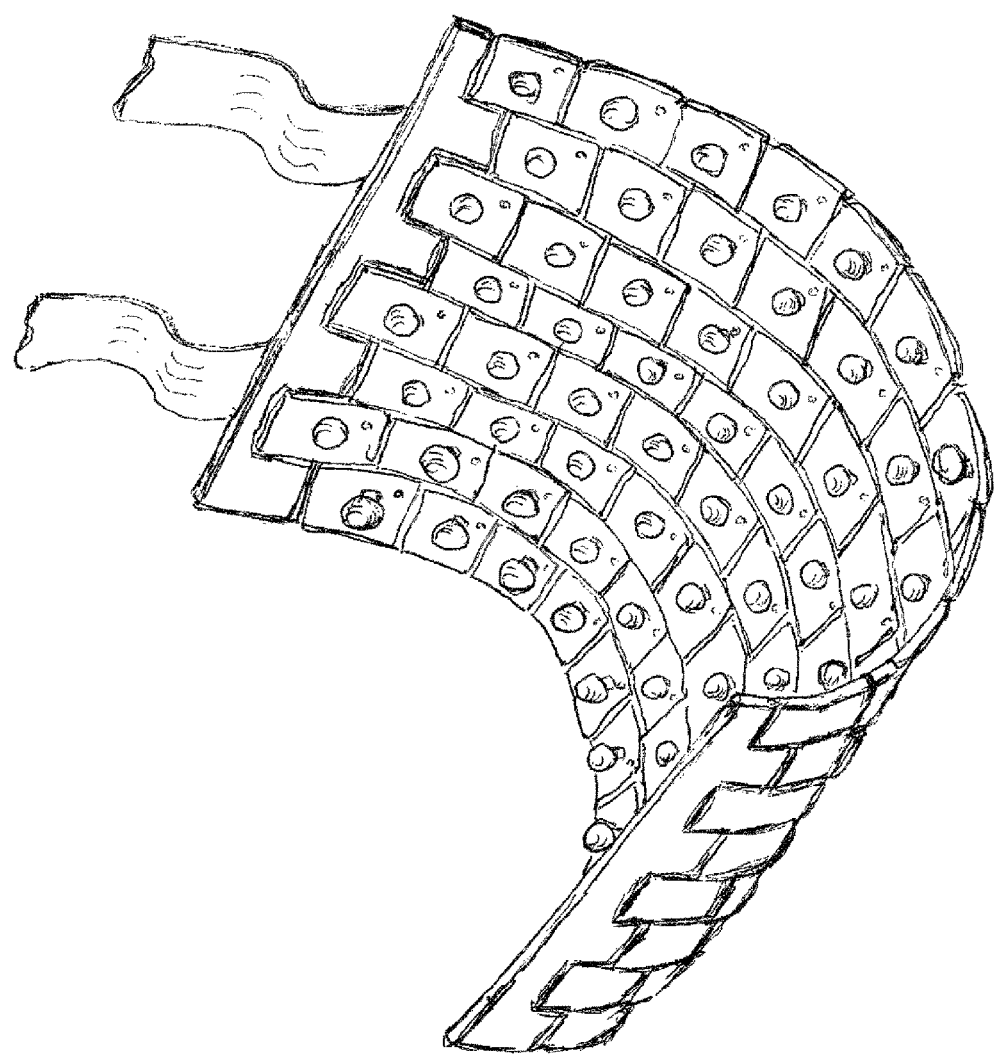
Figure 12:
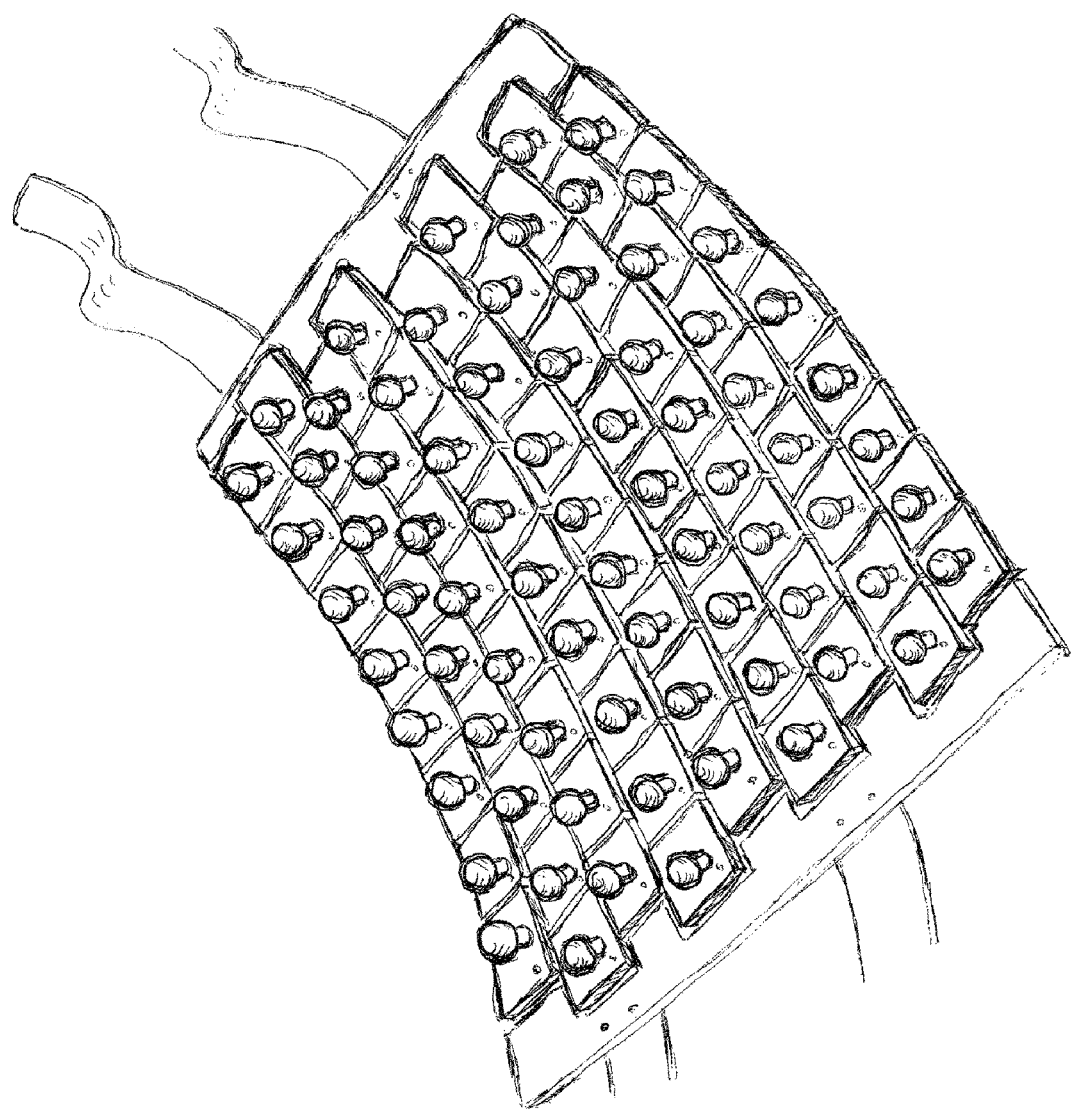

FIGS. 10-11 are examples of an energy delivery device (e.g. similar to FIG. 9A) where the 2D array is a sleeve and/or curved sheet. In FIG. 12 the sheet is flatter than as in FIG. 11.

FIG. 10: The Shape of ARM SLEEVE and its basic chain board (one of m×n units).

FIG. 11: The Shape of ARM SLEEVE and its basic chain boards (m×n units).

FIG. 12: The Shape of The Abdomen Applicator and its basic chain boards, (m×n units). (It will combined from two Applicators on one sleeve)

Figure 13:
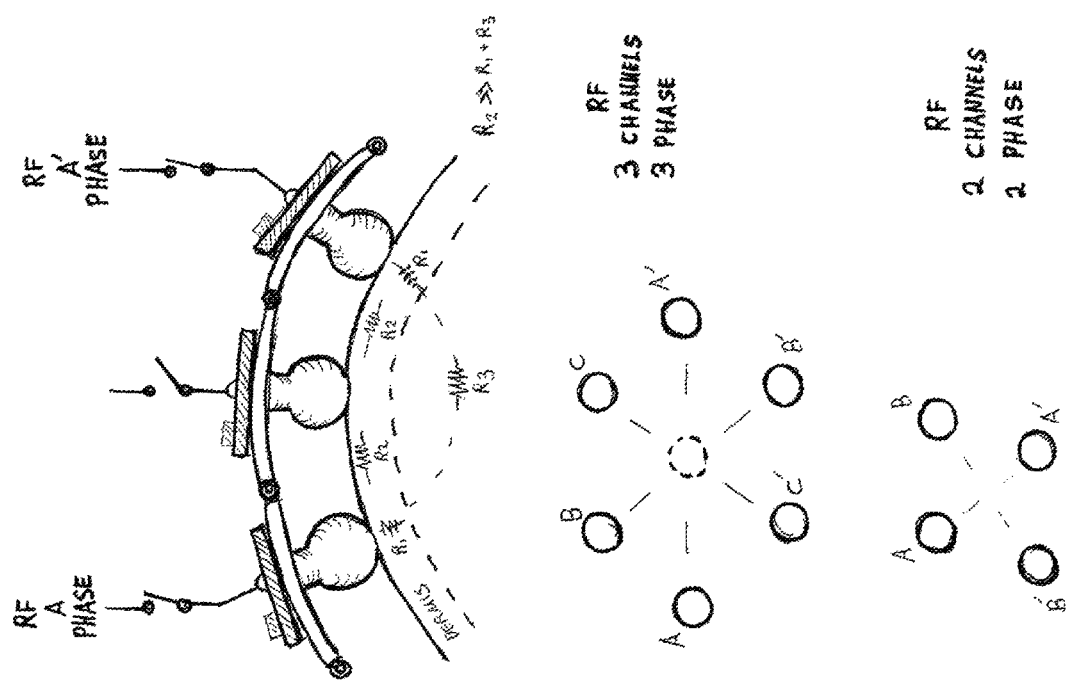
FIGS. 13-14 illustrate arrangements for electrodes.

FIG. 13 illustrates active arrangements—e.g. compare with FIG. 91.

FIG. 13 shows The Shape of the RF/EMS Electrodes and its active arrangement.

The option of 6 active Electrode or 4 active Electrodes. In this example, the Mid Electrode may have no influence on RF action.

Figure 14:
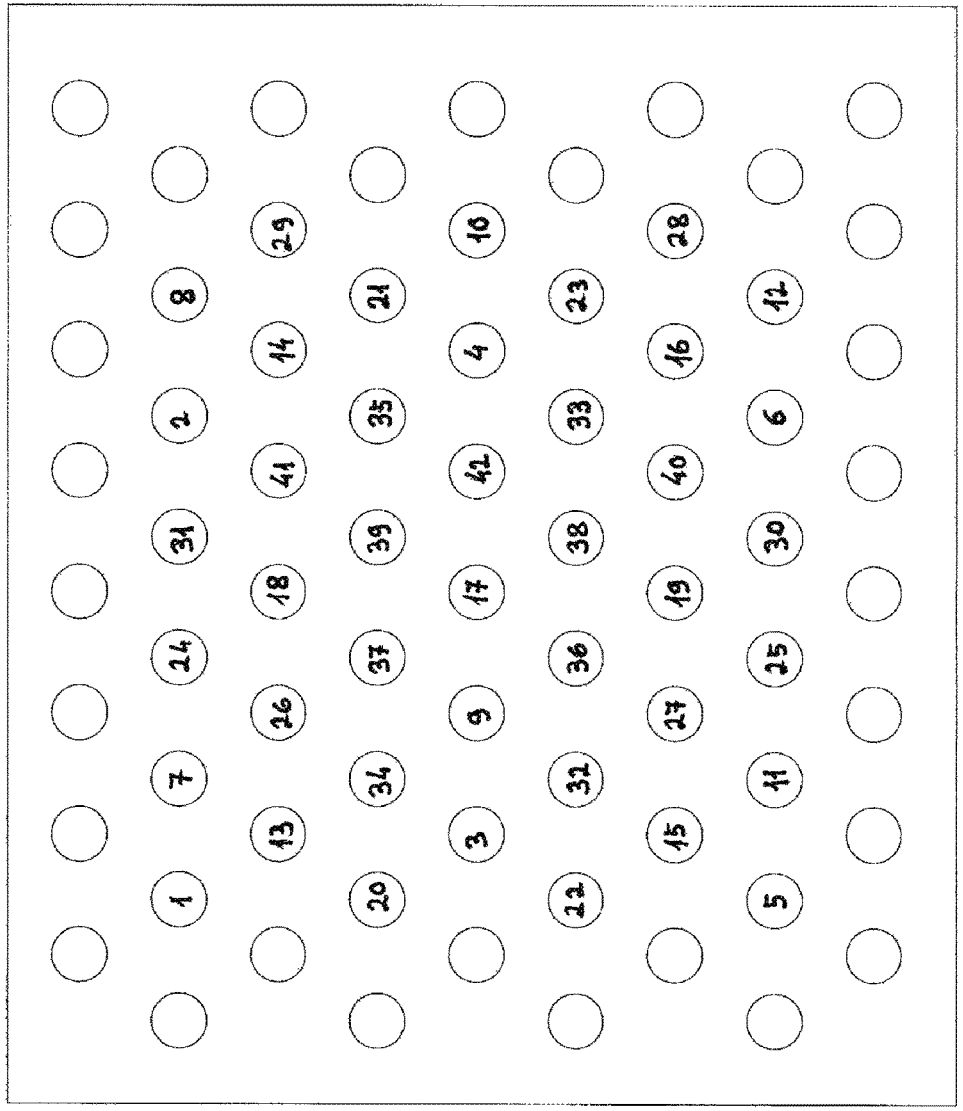

FIG. 14 illustrates many spates and shows how an electrode which is sometimes passive may at other times be active.

FIG. 14 shows the open sleeve Applicator, for example with 70 Electrodes, and 42 Treatment Areas, the numbers show the RF Treated area as an optional sequence and the Treatment order, each number represent six Electrode around it.

Figure 15:
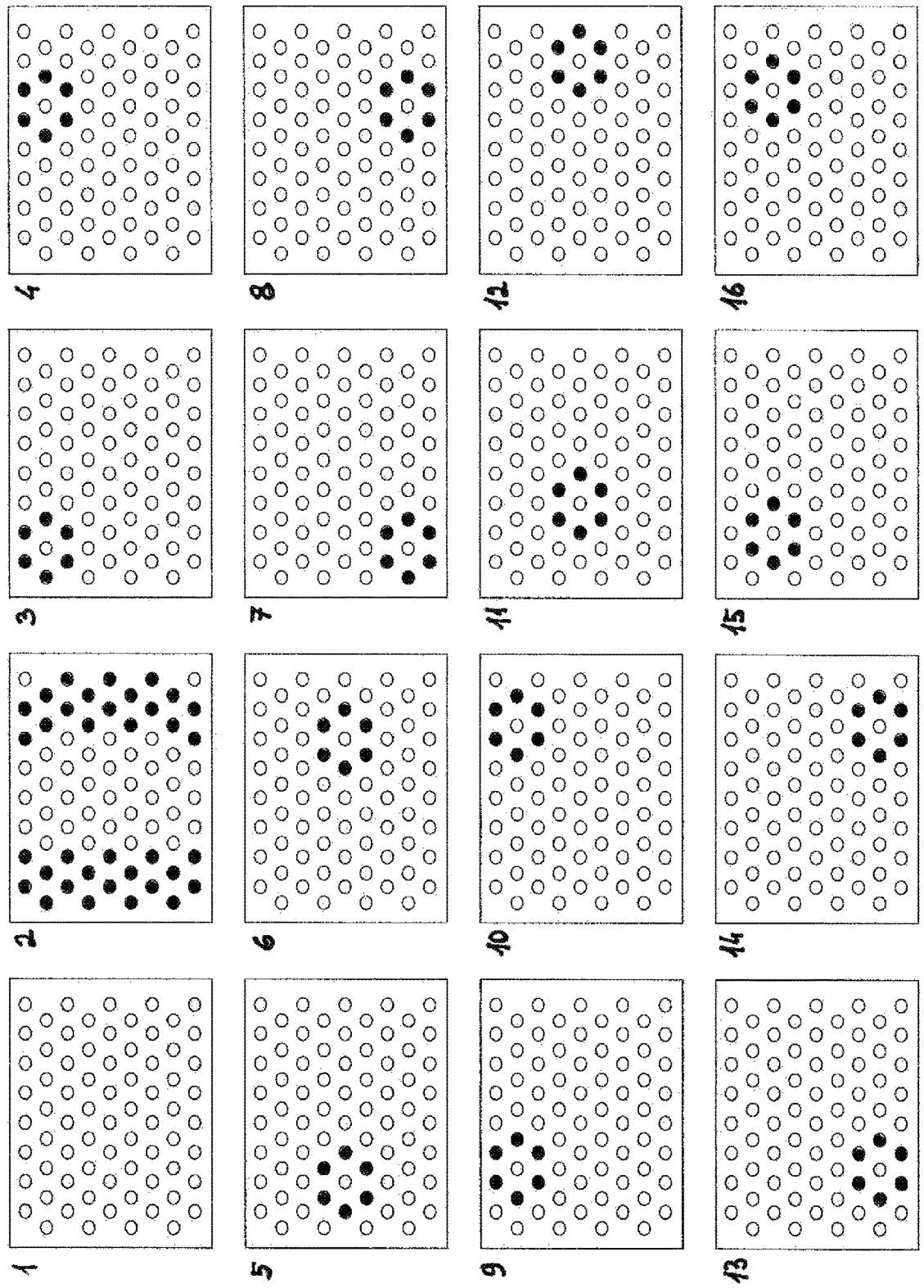
FIG. 15 describes a protocol for delivering energy to biological tissue.

FIG. 15 is similar to FIG. 27G.

FIG. 15 shows: The open sleeve Applicator, for example with 70 Electrodes, and 42 Treatment Areas, the optional sequence and the Treatment order with six active Electrodes, on each state. (Only the 16 first steps are shown).

State #1 is for non active state
State #2 is for EMS Pulsing
State #3 is the RF on limited Area.

FIGS. 16-26 illustrate different form factors of a sleeve (e.g. partial or complete—e.g. closed sleeve or open closable sleeve where the electrodes 210 point inwardly towards a sleeve axis)—the sleeve may have any form factor including but not limited to Knee (e.g. symmetric), elbow, upper arm, Torso Arm Elbow, leg.

Figure 16:
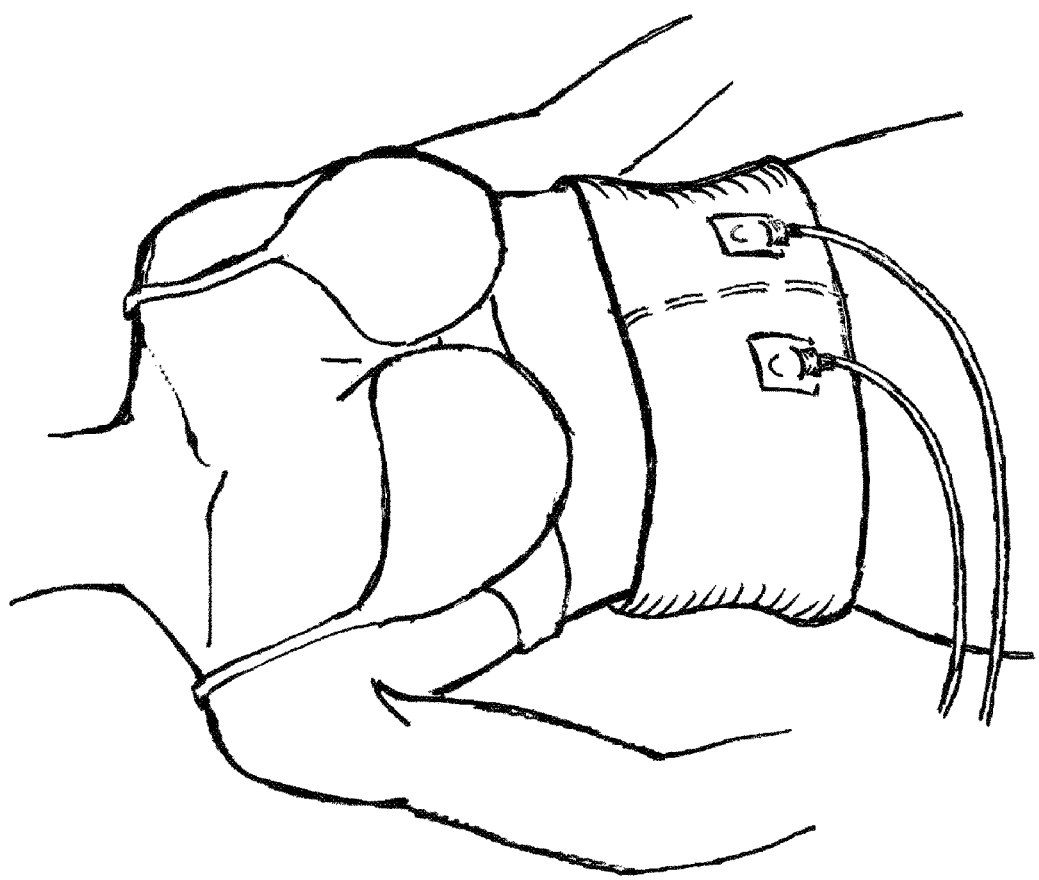

FIG. 16 shows The Women Abdomen Applicators, combined from two Applicators on one sleeve, used for: Flatten Abdomen, For thigh Abdomen, Treat for Body Contouring and Fat Reduction, Fat dissolving, Fat Melting, Remove obstruction from channels and collaterals, Body Shaping, For thigh Waist, Slim Waist, and Reduce Stretch Marks.

Figure 17:
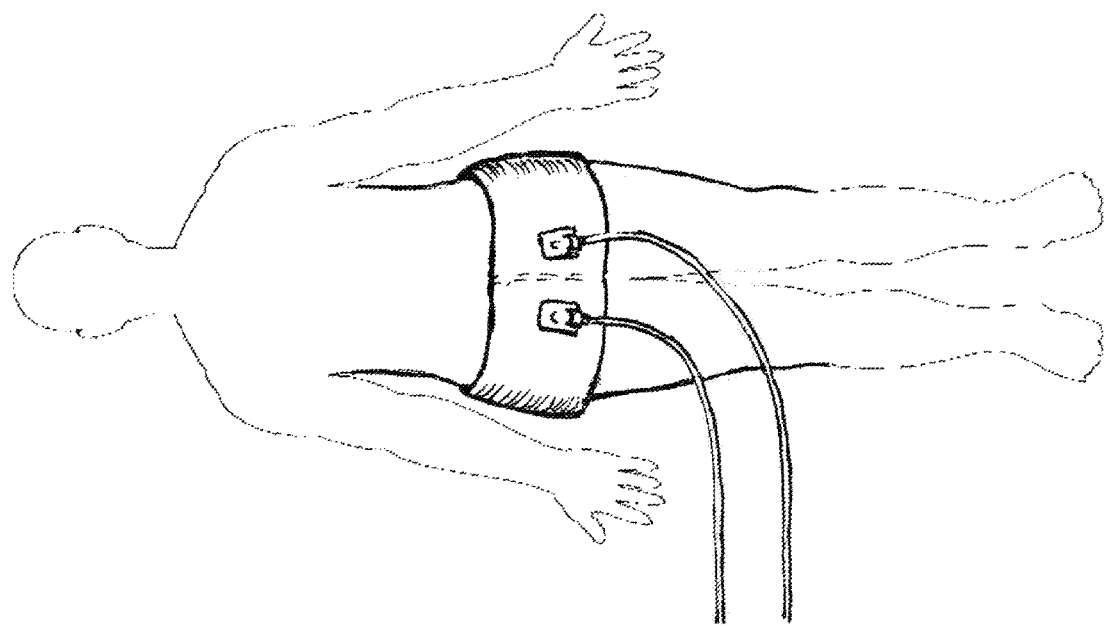
Figure 18:
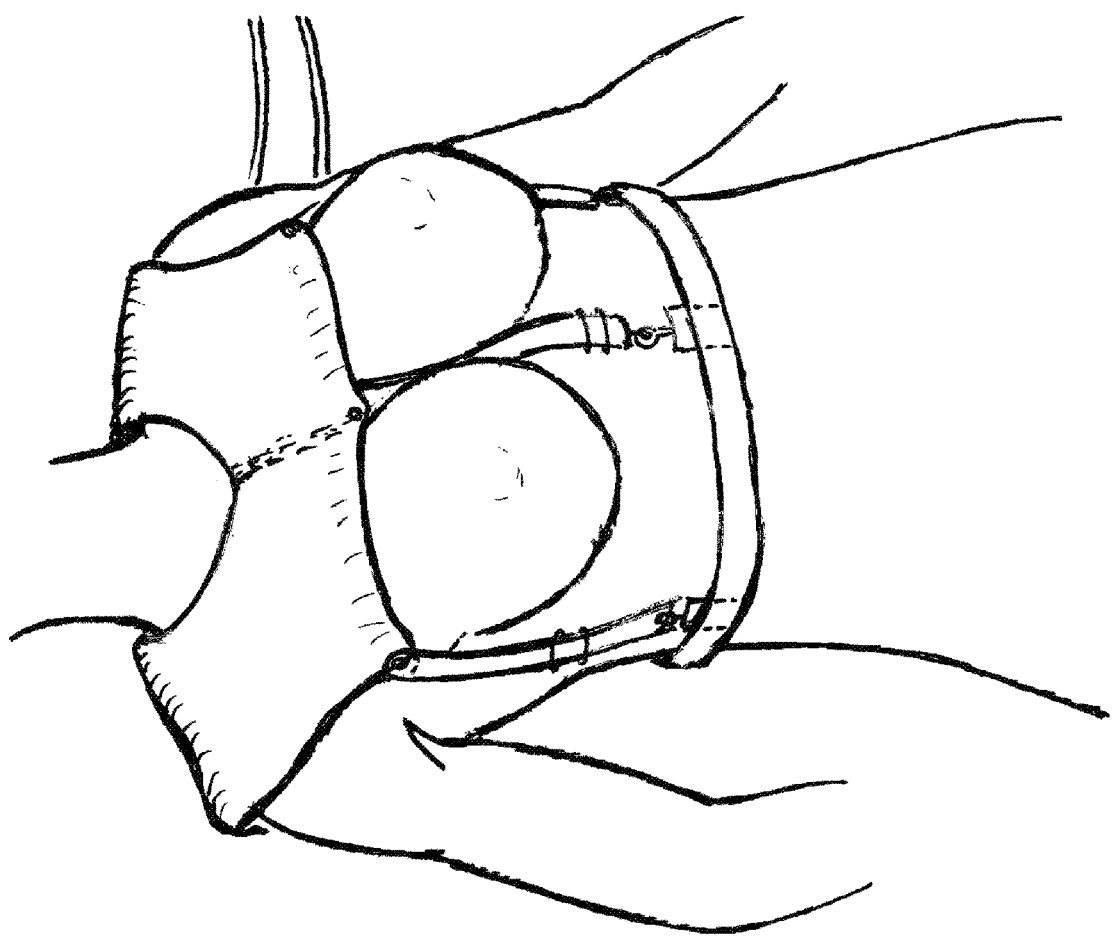

FIG. 17 shows The Men Abdomen Applicators, combined from two Applicators on one sleeve, used for. For example, it will be the same as for Women, used for: Flatten Abdomen, For thigh Abdomen, Treat for Body Contouring and Fat Reduction. Fat dissolving, Fat Melting; Removing obstruction from channels and collaterals; Body Shaping; For thigh Waist, Slim Waist; Reduce Stretch Marks FIG. 18 shows the upper Back and upper chest Applicator, from front view, combine from two Applicators connected on the front and strips, used for: Skin Tightening, Fat dissolving, Fat Melting, Body Shaping, and Reduce Stretch Marks.

Figure 19:
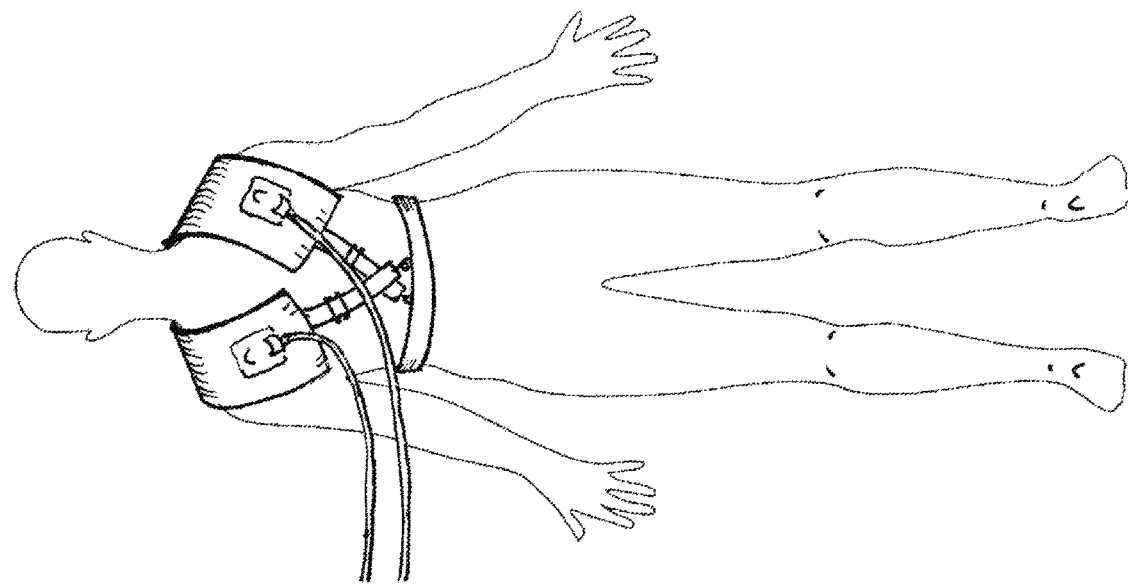
Figure 20:
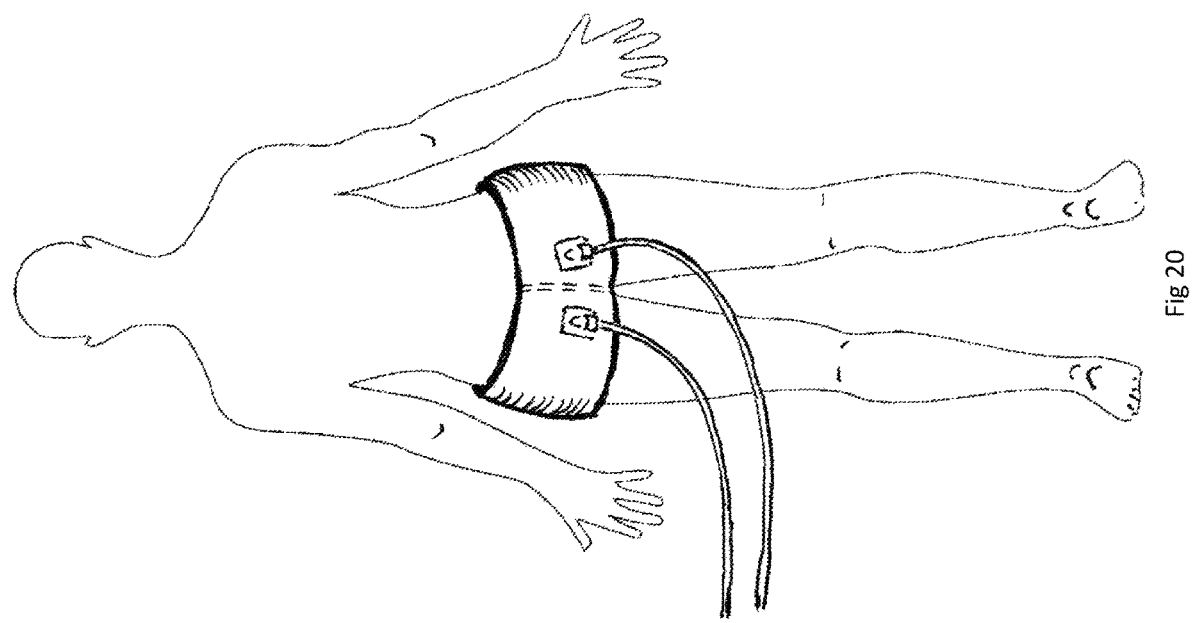

FIG. 19 shows The upper Back and upper chest Applicator, from back view, combine from two Applicators connected on the front and strips, used for: Skin Tightening Fat dissolving, Fat Melting Body Shaping Reduce Stretch Marks FIG. 20 shows The Women Buttocks Applicators, combine from two Applicators on on sleeve. It may be the same as for Abdomen, used for: For thigh Bell; For thigh Waist, Slim Waist; Fat dissolving, Fat Melting; and reducing Stretch Marks.

Figure 21:
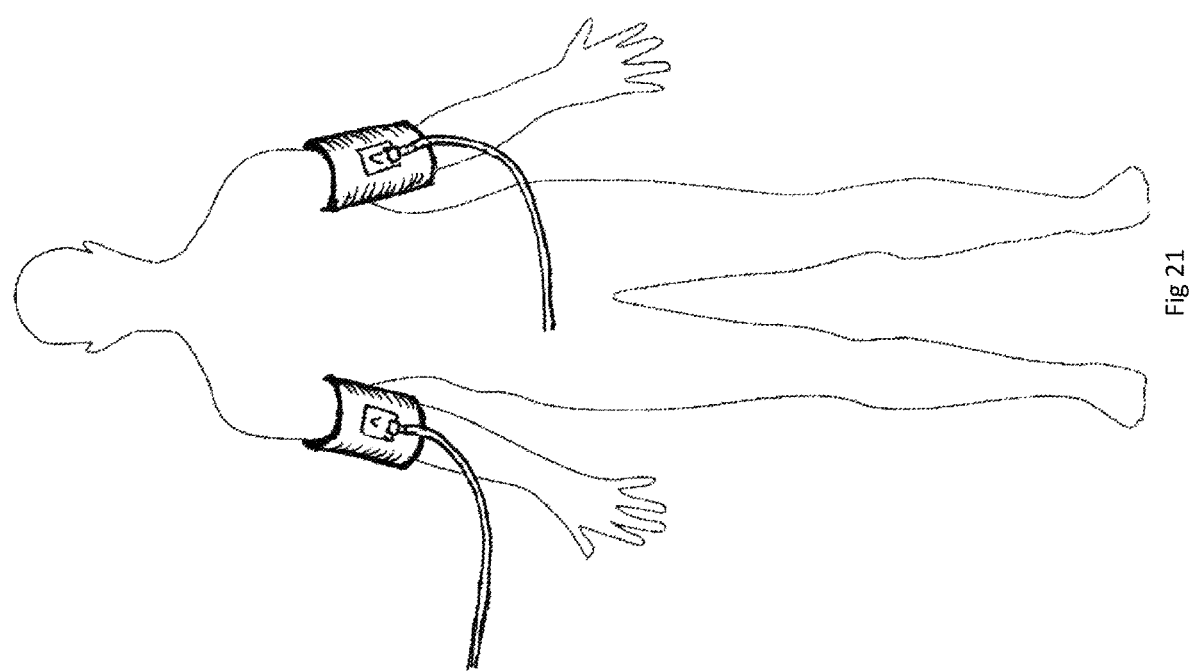
Figure 22:
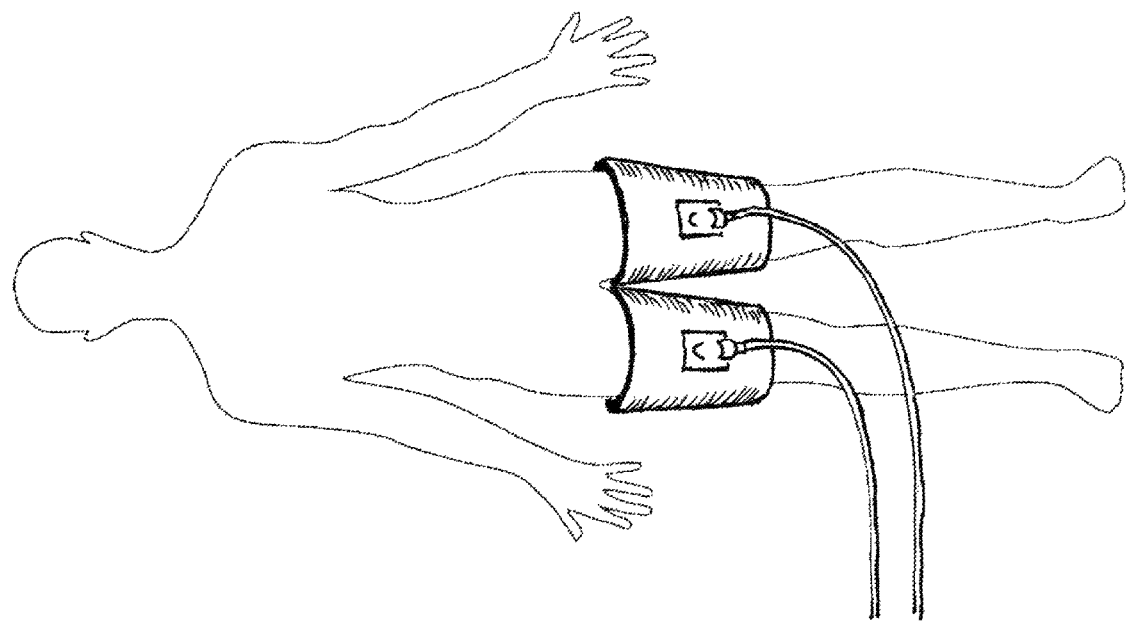
Figure 23:
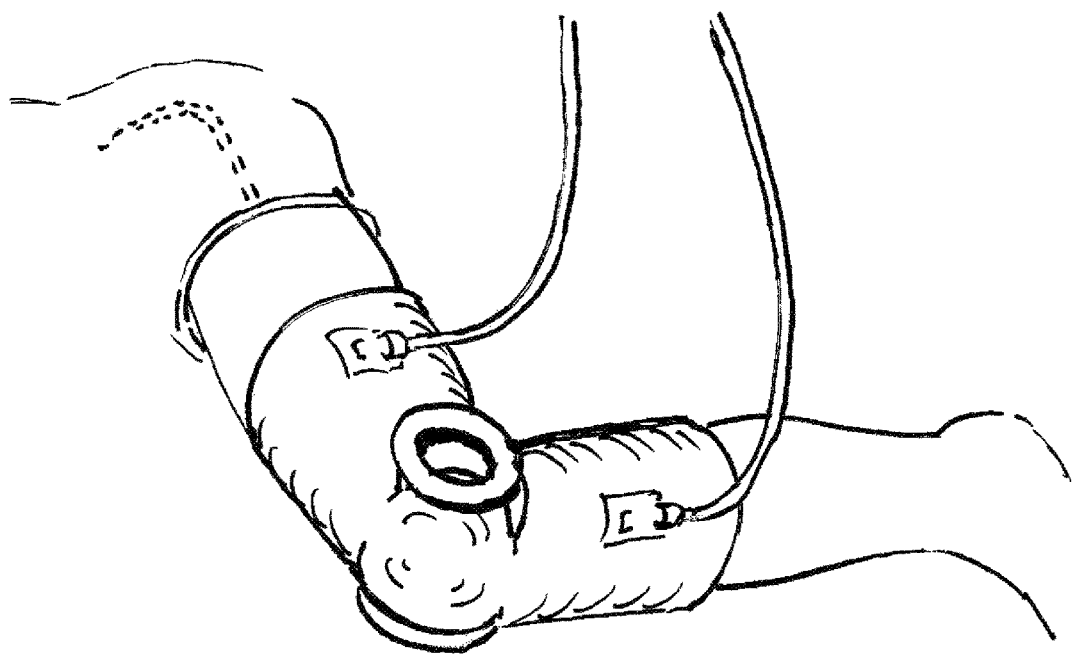

FIG. 21 shows The arm Applicators, use two sleeve Applicators that operate on the same time, used for: For thigh Arms; Thin Arms; Fat dissolving, Fat Melting FIG. 22 shows the LEG Applicators, used two sleeve Applicators that operate on the same time, used for: Treat for Body Contouring; Fat Reduction; Fat dissolving, Fat Melting; Leg sliming; Eliminate Cellulite; cellulite reduction; and Reducing Stretch Marks FIG. 23 shows The KNEE Applicators, use two sleeve Applicators that operate on the same time and with Magnetic coils for the PEMT option, used for broken Bones wound Therapy.

Figure 24:
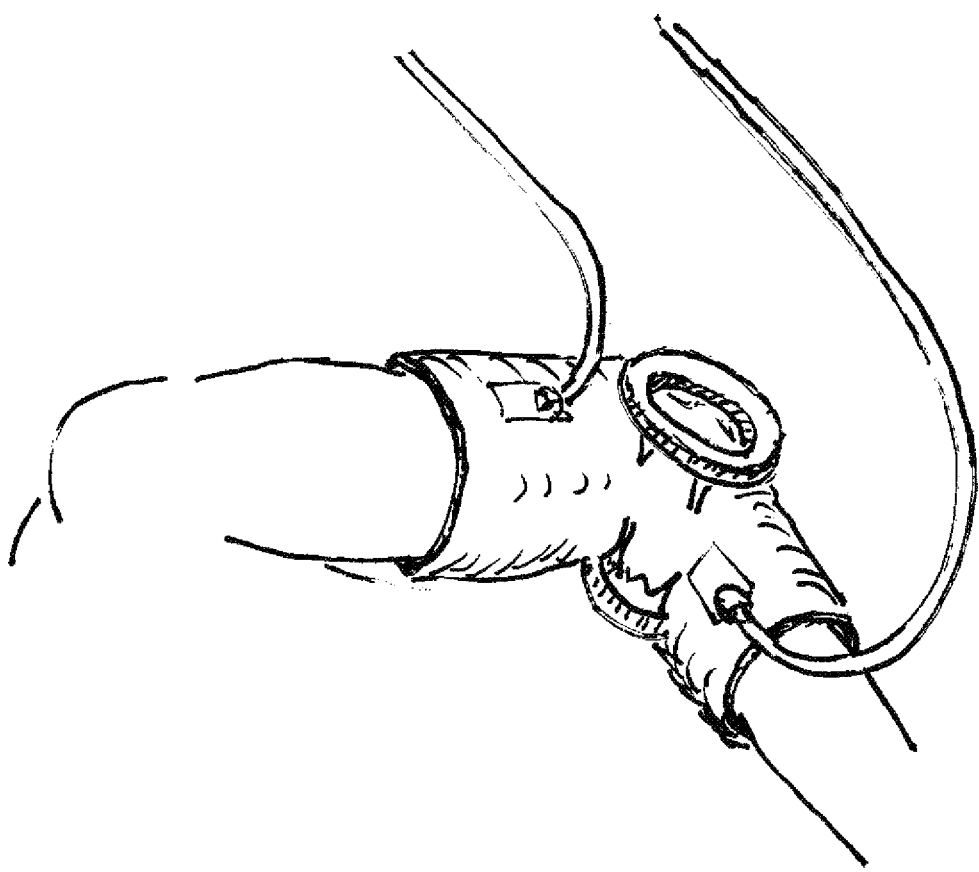

FIG. 24 shows The ELBOW Applicators, use two sleeve Applicators that operate on the same time and with Magnetic coils for the PEMT option, used for: Broken Bones wound Therapy.

Figure 26:
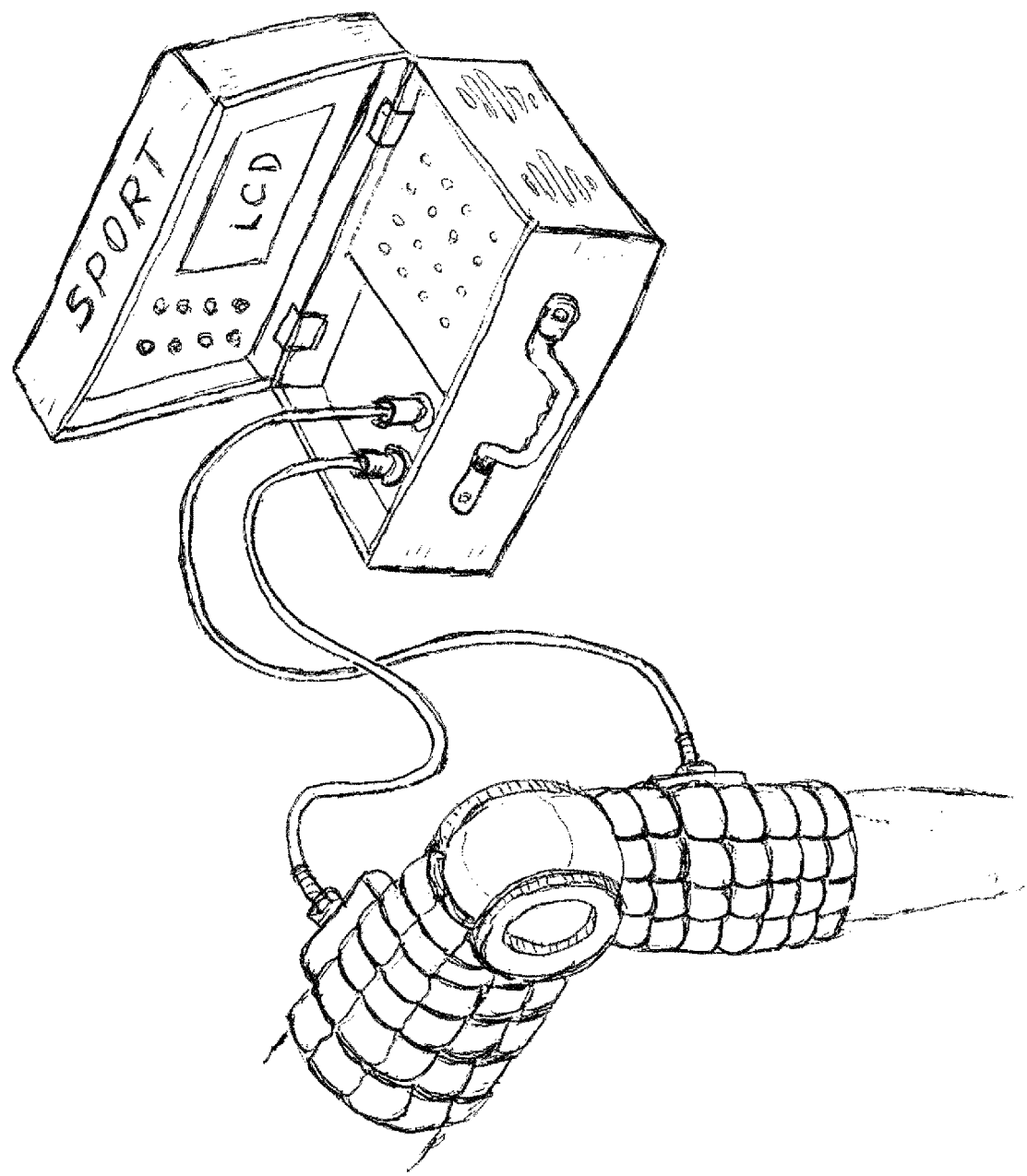

FIG. 25 shows the SAFE Control Sleeve on the ARM and the MAIN CONTROL MODULE in the KNAPSACK version that allow mobility, and LEG Applicators for example, used for: Skin Tightening for whole body, the user can move around, Treat for Body Contouring and fat reduction, the user can move around FIG. 26 shows The MAIN CONTROL MODULE in the Suitcase version that allow mobility, and LEG Applicators for example, used for: Sport Injury First Aid Home Use—for example, it may works on a rechargeable Battery, and/or allow a lower energy).

Additional Discussion

Some embodiments relate to an RF energy-delivery device comprising:
a. a plurality of electrically-insulating plates that are flexibly connected to each other to form a flexible and/or malleable sheet or sleeve or 2D array of plates defining first and second sides on facing away from each other;
b. a plurality of RF electrodes, each RF electrode extending from a respective plate on the first side thereof;
c. an RF node-matrix comprising:
   i. plurality of parallel RF voltage lines; and
   ii. a plurality of control-signal lines, the RF voltage lines and control signal lines defining a two-dimensional array of control nodes such that two or more RF voltage lines pass through each control node, each RF electrodes of the plurality of RF electrodes being resident at a different respective control-node;
   iii. a plurality of switches, wherein each RF-electrode-hosting control-node includes a respective plurality of switches for specifying (A) if the electrode hosted at the control node is connected to one of the RF voltage lines passing through the control node and (B) if so, which one of the RF voltage lines;
d. an address driver MUX controller for sending control signals via each of the control-signal lines to control the switches to specify for each RF-electrode-hosting-control node (A) if the electrode hosted at the control node is connected to one of the RF voltage lines passing through the control node and (B) if so, which one of the RF voltage lines;
e. a plurality of RF channels, each RF channel defining an RF signal having first and second poles; and
f. a switching matrix configured to apply each RF channel, at any given time, to a selected pair of the RF voltage lines so that the switching matrix, together with the MUX controller selectively activates the electrodes with RF energy to define, at any given time, multiple opposite-pole pairs of the electrodes.

In some embodiments, the further comprising:

An EMS channel defines an high-voltage low-frequency square EMS signal, wherein the MUX and the switching matrix give us are configured to deliver EMS muscle stimulation.

Thus, the device may operate in RF mode and in EMS mode—as shown in FIG. 18, it is possible for example (see FIG. 18) to switch back and forth between EMS mode (e.g. square pulses—e.g. at a frequency of at most 20 Hz or at most 15 Hz or at most 10 Hz) and RF mode (e.g. a frequency of at least 5 MHz or at least 10 MHz or at least 20 MHz). In the RF and/or the EMS mode according to example embodiments, the pulse amplitude may be at least 30 volts or at least 50 volts or at least 100 volts.

Alternatively or additionally, LEDs and/or dioate lasers 240 (see FIG. 9D) may deliver optical radiation—e.g. PWM modifies the duty cycle—pulse width 1-100 milliseconds; variable frequency—20 Hz or more; e.g. each LED has an average power of at least 100 milli-watts or at least 200 milli-watts and/or at most 1 Watt.

Alternatively or additionally, the device is configured to deliver pulsed magnetic therapy, pulse magnetotherapy, or PEMF. (see FIG. 18—where "PEMF" is labeled as "PEMS").

Some embodiments relate to a sleeve defining a central axis+one or more types of energy devices (a plurality of energy-emitters—e.g. LED or VCSELs) configured to inwardly deliver energy (aesthetics and/or therapeutics) from an inner surface of the sleeve towards the central axis to treat tissue.

Some embodiments relate to a hybrid energy-delivery device comprising: a. a plurality of electrically-insulating 204 plates (e.g. rigid or semi-rigid) that are flexibly connected to each other to form a flexible and/or malleable sheet or sleeve or 2D array of plates defining first and second surfaces on facing away from each other; b. a plurality of electrodes 210, each extending from a respective electrically insulating plate (e.g. the first side of the sheet) c. an electrical controller configured to operate the electrodes to provide at least of, or any combination of the following modes: RF mode, EMS mode and TENS mode.

Some embodiments relate to an hybrid energy-delivery device comprising: a. a plurality of electrically-insulating plates that are flexibly connected to each other to form a flexible and/or malleable sheet or sleeve or 2D array of plates defining first and second surfaces on facing away from each other; b. a plurality of electrodes, each extending from a respective electrically insulating plate (e.g. the first side of the sheet) c. control circuitry configured to select one or more pair(s) of the electrodes and to operate them in opposite polarity so as to deliver RF power from each selected pair of electrode.

Some embodiments relate to a hybrid energy-delivery device comprising: a. a plurality of electrically-insulating plates that are flexibly connected to each other to form a flexible and/or malleable sheet or sleeve or 2D array of plates defining first and second surfaces on facing away from each other; b. a plurality of electrodes, each extending from a respective electrically insulating plate (e.g. the first side of the sheet) c. a plurality of laser diodes each extending from a respective plate in the same direction as the electrodes. In different embodiments, the device is configured to deliver energy according to temperature sensor(s) 244. For example, the device may operate to establish a relatively uniform temperature—e.g. more energy is delivered via electrodes 210 where the respective temp sensor 244 indicates a lower temperature and less energy is delivered via electrodes 210 where the respective temp sensor 244 indicates a lower temperature. E.g. the device may maintain a maximum temperature of the biological tissue to at most 45 or at most 44 or at most 43 or at most 42 degrees Celsius.

In embodiments, any combination of the features are provided: Switching address; in response to temperature data; e.g. to require temperature of a least 35 degrees and at most 42 degrees; closable sleeve (e.g closable by Velcro); electrodes have rounded end; ball and/or dome and/or spherical and/or hemi-spherical electrodes.

In some embodiments, each individual Plate 204 has an area of between 5 cm^2 and 25 cm^2 e.g. at most 15 cm^2 or at most 10 cm^2—for example, the plate has an area of 9 cm^3. In some embodiments, a distance between neighboring electrodes is at least 2 cm and at most 15 cm.

Knee Sleeve

In different embodiments, each plate 204 may be malleable and/or flexible and/or the 2D-sleeve is a sheet or slab. For example, an aggregate of semi-flexible or bendable 2D array of plates—flat 2D array or a curved 2D array.

In embodiments, it includes LLLT (e.g. VSel—laser (e.g. diode laser)), RF electrode also for TENS and/or EMS and/or RF+PEMF. It may implement an algorithm for coverage—e.g. to slowly heat to a uniform temperature.

It may include a 2D-array of plates shaped like a knee sleeve and/or a 2D-array of plates shaped like a temperature sensor.

It may provide adaptive heating based on a target of uniform temperature can jump around.

In some embodiments, the device treats fibromyalgia.

In some embodiments the device is battery-powered—With a battery (light and portable device) energy is scarce and yet there may be a high energy/power requirement to deliver sufficient power/energy to achieve a biological treatment goal.

Figure 28A:
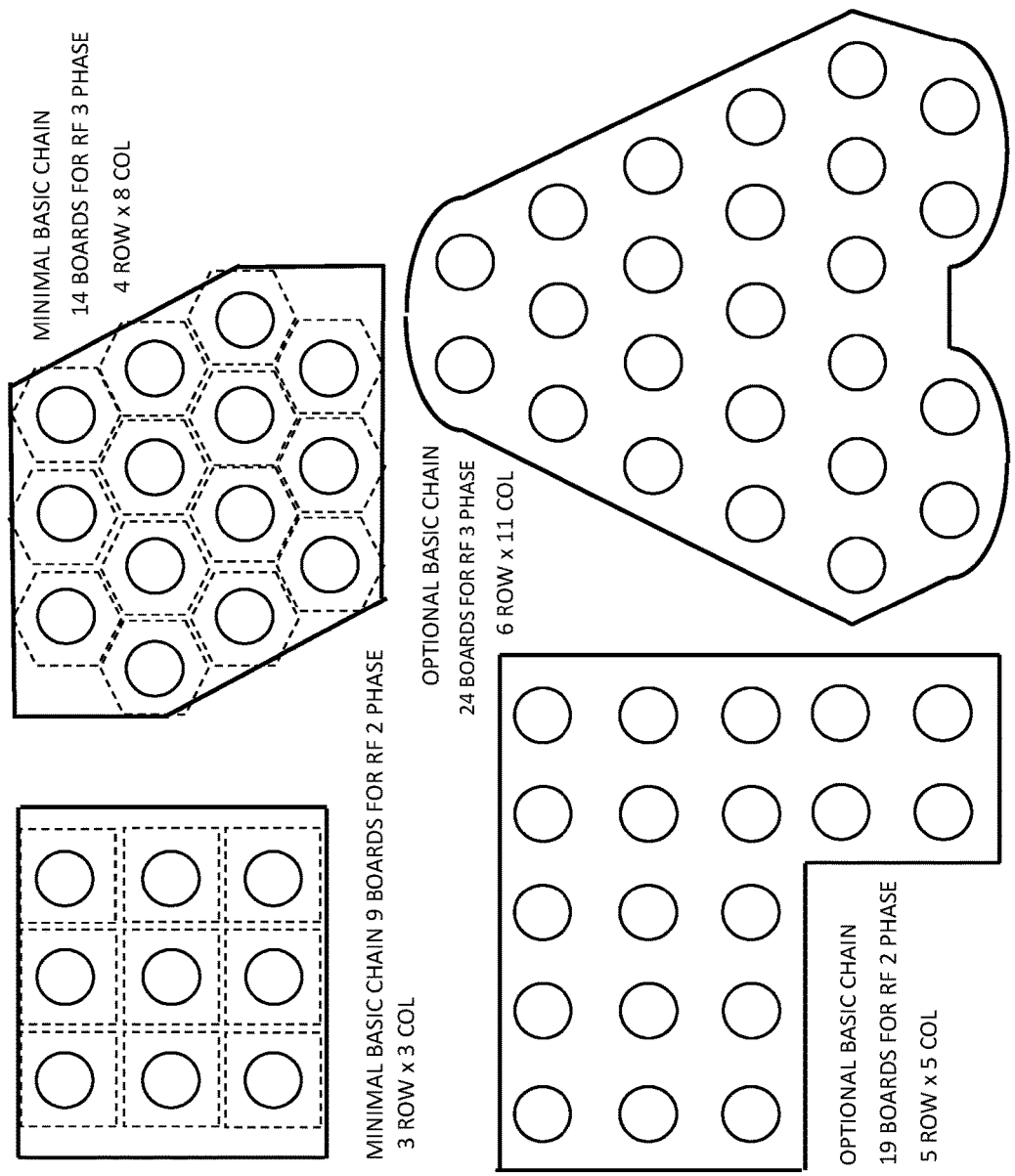
FIG. 28A illustrates basic chain board options for 2 phase and/or 3 phase sleeve applicators.

FIG. 28A illustrates basic chain board options for 2 phase and/or 3 phase sleeve applicators. In some embodiments, the model of FIG. 28A or FIG. 28B. allows to build an assembly of basic units having any size and/or any shape within the numerical range permitted by the address scheme.

FIG. 28B describes a method of temperature simultaneous measurements from the whole treatment area for 2 phase and/or 3 phase sleeve applicators It is further noted that any of the embodiments described above may further include receiving, sending or storing instructions and/or data that implement the operations described above in conjunction with the figures upon a computer readable medium. Generally speaking, a computer readable medium (e.g. non-transitory medium) may include storage media or memory media such as magnetic or flash or optical media, e.g. disk or CD-ROM, volatile or non-volatile media such as RAM, ROM, etc.

Having thus described the foregoing exemplary embodiments it will be apparent to those skilled in the art that various equivalents, alterations, modifications, and improvements thereof are possible without departing from the scope and spirit of the claims as hereafter recited. In particular, different embodiments may include combinations of features other than those described herein. Accordingly, the claims are not limited to the foregoing discussion.

What is claimed is:

1. An energy-delivery device for delivering multi-type electromagnetic pulses of energy to a tissue, comprising:
   a) a plurality of individually controlled electrodes, flexibly connected to each other to form a flexible and/or malleable sheet or sleeve or 2D array for covering a desired area of said tissue, each of said electrodes comprises:
      a.1) an electrically-insulating plate;
      a.2) an electromagnetic electrode extending from said plate on a first side thereof, for delivering electromagnetic energy at predetermined frequencies to said tissue;
      a.3) an optical emitter for delivering optical energy at predetermined wavelengths to said tissue, during time periods when electromagnetic energy is delivered;
      a.4) a temperature sensor, being part of said electrode, for sensing a temperature of the tissue being in contact with said electrode during energy delivery along an entire treatment period;
   b) a controller, which is adapted to:
      b.1) test a quality of contact between each said electrode and said tissue by measuring impedances between predetermined pairs of said electrodes;
      b.2) selectively activate pairs of the electrodes having sufficiently low impedance therebetween, to define, at any given time, multiple opposite-pole pairs of the electrodes, and to deliver via said pairs of opposite-poles, a combination of electromagnetic and optical energy pulses to said tissue,
      wherein each of said opposite pole pairs are sequentially activated in groups of six electrodes consisting of three pairs of opposing electrodes symmetrically separated from each other and such that each pair is excited by alternating power derived from signals that are shifted in phase with respect to each other by about 120 degrees or,
      wherein each of said opposite pole pairs are sequentially activated in groups of four electrodes consisting of two pairs of opposing electrodes symmetrically separated from each other and such that each pair is excited by alternating power derived from signals that are shifted in phase with respect to each other by about 90 degrees;
      b.3) continuously sense the temperature of the tissue below each electrode and deactivate a group of electrode pairs, below which the sensed temperature exceeds a predetermined threshold.

2. The energy-delivery device according to claim 1, in which the controller is implemented by an electromagnetic node-matrix, which comprises:
   a) plurality of parallel electromagnetic energy voltage lines; and
   b) a plurality of control-signal lines, the electromagnetic voltage lines and control signal lines defining a two-dimensional array of control nodes such that two or more electromagnetic voltage lines pass through each control node, each electromagnetic electrode of the plurality of electromagnetic electrodes being addressable and resident at a different respective control-node;
   c) a plurality of switches, wherein each of addressable electromagnetic-electrode-hosting control control-node includes a respective plurality of switches for specifying (A) if the electrode hosted at the control node is connected to one of the electromagnetic voltage lines passing through the control node and (B) if so, which one of the electromagnetic voltage lines;
   d) an address driver MUX controller for sending control signals via each of the control-signal lines to control the switches to specify for each said electromagnetic-electrode-hosting-control node (A) if the electrode hosted at the control node is connected to one of the electromagnetic voltage lines passing through the control node and (B) if so, which one of the electromagnetic voltage lines;
   e) a plurality of electromagnetic channels, each electromagnetic channel defining an electromagnetic signal having first and second poles; and
   f) a switching matrix configured to apply each electromagnetic channel, at any given time, to a selected pair of the electromagnetic voltage lines so that the switching matrix, together with the MUX controller selectively activates the electrodes with electromagnetic energy to define, at any given time, multiple opposite-pole pairs of the electrodes.

3. The energy-delivery device according to claim 1, in which each electrode further comprises a magnetic coil for the delivery of therapeutic magnetic energy to the tissue in the form of a Pulsed Electromagnetic Field (PEMF).

4. The energy-delivery device according to claim 1, in which the electromagnetic energy consists of Electrical Muscle Stimulation (EMS) pulses.

5. The energy-delivery device according to claim 1, in which the electromagnetic energy consists of Transcutaneous Electrical Nerve Stimulation, (TENS) pulses.

6. The energy-delivery device according to claim 1, in which the 2D array is divided to two symmetric sub-arrays, such that the electrodes of one sub-array are activated at time slots during which the electrodes of the other sub-array are inactive, and vice versa, or both sub-arrays are activating during the same time.

7. The energy-delivery device according to claim 1, in which groups of electrodes in the array of are activated in a predetermined sequence, according to which RF energy is delivered first to colder tissue areas.

8. The energy-delivery device according to claim 1, in which different pairs of electrodes are activated by RF signals having phase delay between them.

9. The energy-delivery device according to claim 6, in which a sequence is determined according to a desired overlap between treated tissue areas.

10. The energy-delivery device according to claim 2, in which the electromagnetic energy is RF, TENS or EMS energy or any combination thereof.

11. The energy-delivery device according to claim 1, in which energy is delivered to the tissue periodically, where in each period, first applying EMS energy, followed by RF energy, while at the same time of applying RF energy, applying also optical energy, for heating said tissue.

* * * * *